(12) United States Patent
Henning et al.

(10) Patent No.: US 12,305,148 B2
(45) Date of Patent: May 20, 2025

(54) SILOXANES FOR TREATING TEXTILES AND FOR USE IN CLEANING AND CARE FORMULATIONS

(71) Applicant: Evonik Operations GmbH, Essen (DE)

(72) Inventors: Frauke Henning, Essen (DE); Jörg Peggau, Essen (DE); Andrea Lohse, Bottrop (DE); Astrid Zündorff, Muelheim an der Ruhr (DE); Sarah Radloff, Bochum (DE); Alexandra Trambitas, Alzenau (DE)

(73) Assignee: Evonik Operations GmbH, Essen (DE)

( * ) Notice: Subject to any disclaimer, the term of this patent is extended or adjusted under 35 U.S.C. 154(b) by 1238 days.

(21) Appl. No.: 15/733,704

(22) PCT Filed: Mar. 26, 2019

(86) PCT No.: PCT/EP2019/057491
§ 371 (c)(1),
(2) Date: Sep. 30, 2020

(87) PCT Pub. No.: WO2019/192876
PCT Pub. Date: Oct. 10, 2019

(65) Prior Publication Data
US 2021/0047591 A1   Feb. 18, 2021

(30) Foreign Application Priority Data

Apr. 3, 2018   (EP) .................................... 18165408

(51) Int. Cl.
*C11D 3/37* (2006.01)
*A61Q 19/10* (2006.01)
*C08G 77/26* (2006.01)
*C08K 5/17* (2006.01)

(52) U.S. Cl.
CPC ............ *C11D 3/3742* (2013.01); *A61Q 19/10* (2013.01); *C08G 77/26* (2013.01); *C08K 5/17* (2013.01)

(58) Field of Classification Search
CPC ................................................... C08G 18/61
See application file for complete search history.

(56) References Cited

U.S. PATENT DOCUMENTS

| | | |
|---|---|---|
| 4,891,166 A | 1/1990 | Schaefer et al. |
| 4,921,895 A | 5/1990 | Schaefer et al. |
| 5,248,783 A | 9/1993 | O'Lenick |
| 5,578,692 A | 11/1996 | Biggs et al. |
| 7,834,122 B2 | 11/2010 | Ferenz et al. |
| 7,964,694 B2 | 6/2011 | Ferenz et al. |
| 8,557,944 B2 | 10/2013 | Henning et al. |
| 8,598,295 B2 | 12/2013 | Henning et al. |
| 8,778,319 B2 * | 7/2014 | Herrwerth ................. C07F 7/10 424/70.122 |
| 9,138,385 B2 * | 9/2015 | Dahl ........................ A61Q 5/12 |
| 9,346,919 B2 | 5/2016 | Jaskewitsch et al. |
| 9,481,695 B2 | 11/2016 | Knott et al. |
| 9,695,202 B2 | 7/2017 | Henning et al. |
| 10,266,658 B2 | 4/2019 | Henning et al. |
| 2010/0184634 A1 | 7/2010 | Henault et al. |
| 2012/0168664 A1 | 7/2012 | Maurer et al. |
| 2012/0282210 A1 | 11/2012 | Henning et al. |
| 2012/0294819 A1 | 11/2012 | Herrwerth et al. |
| 2013/0259821 A1 | 10/2013 | Henning et al. |
| 2014/0134125 A1 | 5/2014 | Dahl et al. |
| 2014/0303065 A1 | 10/2014 | Jaskewitsch et al. |
| 2015/0080593 A1 | 3/2015 | Henning et al. |

FOREIGN PATENT DOCUMENTS

| | | |
|---|---|---|
| CN | 102549046 | 7/2012 |
| CN | 102711715 | 10/2012 |
| CN | 105367800 | 3/2016 |
| DE | 37 19 086 | 10/1988 |
| DE | 38 02 622 | 8/1989 |
| DE | 10 2009 029 450 | 3/2011 |
| DE | 10 2010 000 993 | 7/2011 |
| DE | 10 2010 001 531 | 8/2011 |
| DE | 10 2011 078 382 | 1/2013 |
| EP | 2 176 319 | 6/2011 |
| EP | 2 648 695 | 10/2013 |
| EP | 2 789 642 | 10/2014 |
| WO | 2011/032797 | 3/2011 |

(Continued)

OTHER PUBLICATIONS

ACS (Molecule of the week archive: Polydimethylsiloxane, Apr. 14, 2014) (Year: 2014).*
European Search Report issued Oct. 19, 2018 in EP18165408.8, 6 pages.
International Search Report issued Jun. 24, 2019 in PCT/EP2019/057491, 6 pages.
Written Opinion issued Jun. 24, 2019 in PCT/EP2019/057491, 7 pages.
U.S. Appl. No. 13/992,311, filed Jun. 7, 2013, 2013/0259821, Henning et al.
U.S. Appl. No. 13/521,351, filed Jul. 10, 2012, 2012/0282210, Henning et al.
U.S. Appl. No. 16/650,344, filed Mar. 24, 2020, Trambitas et al.
Chinese Office Action dated Mar. 23, 2022 in Chinese Application No. 201980024092.8, 12 pages.
Argentine Examination Report dated Aug. 24, 2022, in Argentine Application No. 20190100868, 4 pages.

*Primary Examiner* — Mark V Stevens
*Assistant Examiner* — Alparslan Asan
(74) *Attorney, Agent, or Firm* — Grüneberg and Myers PLLC

(57) ABSTRACT

Specific siloxanes, compositions containing these specific siloxanes, and processes for preparation thereof, are useful for treatment of fabrics, in cleaning and care formulations for the household and for industrial purposes, and in cosmetic, pharmaceutical and dermatological compositions, especially in cosmetic cleansing and care formulations, hair treatment products and hair aftertreatment products, and for cleaning and care of hard surfaces, preferably for cleaning and care of motor vehicles, especially as additive in drying aids for carwash facilities.

23 Claims, No Drawings

(56) References Cited

FOREIGN PATENT DOCUMENTS

| WO | 2011/088937 | 7/2011 |
| WO | 2012/076293 | 6/2012 |
| WO | 2013/000592 | 1/2013 |

\* cited by examiner

SILOXANES FOR TREATING TEXTILES AND FOR USE IN CLEANING AND CARE FORMULATIONS

CROSS-REFERENCE TO RELATED APPLICATIONS

This application is a National Stage entry under § 371 of International Application No. PCT/EP2019/057491, filed on Mar. 26, 2019, and which claims the benefit of European Application No. 18165408.8, filed on Apr. 3, 2018. The content of each of these applications is hereby incorporated by reference in its entirety.

The invention relates to specific siloxanes, to compositions containing these specific siloxanes, to processes for preparation thereof, and to the use of these compositions for treatment of two-dimensional structures, in cleaning and care formulations for the household and for industrial purposes, and in cosmetic, pharmaceutical and dermatological compositions, especially in cosmetic cleansing and care formulations, hair treatment products and hair aftertreatment products, and for cleaning and care of hard surfaces, preferably for cleaning and care of motor vehicles, especially as additive in drying aids for carwash facilities.

More particularly, the invention relates to hand-modifying active ingredients for treatment of textiles or fabrics which have both higher efficacy and minimized proportions of unwanted by-product constituents of low molecular weight.

Siloxanes or silicones with quaternary ammonium groups (also referred to hereinafter as silicone quats) and the use thereof for finishing of textiles and in cleaning and care formulations are known from the prior art.

Particularly advantageous silicone quats here are those that are obtained by reaction of epoxy-functional siloxanes with tertiary amines. First of all, nucleophilic attack of the tertiary nitrogen of the tertiary amine takes place on the epoxide ring of the epoxy-functional silane, which ultimately leads to ring opening of the epoxide ring. This forms a zwitterion, which is subsequently protonated by a Brønsted acid, giving the silicone quat. Since the epoxy groups are to be converted to a maximum degree, generally stoichiometric amounts of the tertiary amine are used. This can in turn lead to residual amounts of tertiary amines. These residual amounts are undesirable. Residual contents of reactants of low molecular weight, for example the amines used or organic by-products of low molecular weight, can irritate the skin and/or can be sensitizing and/or aquatoxic. On introduction of the silicone quats into aqueous textile treatment liquors, the organic by-products of low molecular weight and the unconverted tertiary amines can dissolve and hence get onto the textile or into the wastewater.

The use of amines that are less of a matter of concern, more particularly cause less or zero skin irritation, sensitization and/or aquatoxicity, generally leads to silicone quats having poorer performance properties. Aqueous emulsions for textile finishing based on the corresponding silicone quats frequently exhibit reduced phase stability/storage stability and/or a poorer assessment of hand in the textile finished therewith.

DE 102010000993 A1 discloses polysiloxanes having at least one quaternary ammonium group. These polysiloxanes are usable in personal cleansing and care products, such as shampoos, hair treatment products and hair aftertreatment products. These polysiloxanes are said to improve both properties such as combability, softness, volume, formability, manageability and disentanglability of undamaged and damaged hair, and impart a pleasing shine to the hair. In the examples are disclosed polysiloxanes that are obtained by reaction of epoxysilanes with amide amines based on fatty acids, namely 3-N,N-dimethylaminopropyfauramide. The exclusive use of amide amines as tertiary amines in the synthesis of these silicone quats leads to a residual content of unconverted amide amines. This is undesirable. There is no disclosure of polysiloxanes having at least one amide ammonium group and also at least one dialkanolammonium group.

DE 102009029450 A1 discloses polysiloxanes having quaternary ammonium groups. These polysiloxanes find use as softeners for fabrics, for example wovens, tissues, nonwovens and/or fibres made of natural and/or synthetic raw materials and/or leather. In the examples are disclosed polysiloxanes that are obtained by reaction of epoxysilanes with amide amines based on coconut fatty acid. Here too, the exclusive use of amide amines as tertiary amines in the synthesis of these silicone quats leads to an undesirable residual content of unconverted amide amines. There is no disclosure of polysiloxanes having at least one amide ammonium group and also at least one dialkanolammonium group.

DE 102011078382 A1 discloses microemulsions including, as oil phase, a polysiloxane containing at least one quaternary ammonium group. In the examples are disclosed polysiloxanes that are obtained by reaction of epoxysilanes with amide amines based on fatty acids. Here too, the exclusive use of amide amines as tertiary amines in the synthesis of these silicone quats leads to an undesirable residual content of unconverted amide amines. There is no disclosure of polysiloxanes having at least one amide ammonium group and also at least one dialkanolammonium group.

DE 102010001531 A1 discloses siloxanes having primary amino functions and organomodified siloxanes having quaternary ammonium functions. There is no disclosure of polysiloxanes having an amide ammonium group or a dialkanolammonium group.

U.S. Pat. No. 5,248,783 discloses the use of amide amines for neutralization of carboxylic acid-functional silicones. There is no disclosure of polysiloxanes having an amide ammonium group or a dialkanolammonium group.

There is also a need to provide siloxanes that have advantages over the prior art.

More particularly, there is a need for siloxanes that are suitable as hand-modifying active ingredients for treatment of textiles or fabrics, and feature high efficacy, but where the proportion of unwanted organic by-products or residual amounts of reactants that irritate the skin and/or are sensitizing and/or aquatoxic has additionally been minimized. There is still a need for siloxanes that lead to improved performance properties, for example improved phase stability/storage stability and/or a better assessment of hand in the textile treated. Frequently, silicone quats settle out on the fabric or textile under alkaline conditions over and above a pH of 9, as may exist during or after the washing of the fabric or textiles. This can lead to spotting, especially when the textiles or fabric are being subjected to a dyeing process. There is therefore still a need for siloxanes that have higher pH stability, especially up to a pH of 11. More particularly, there is a need for skin-friendly and environmentally friendly hand-modifying active ingredients or compositions for the finishing of textile fabrics, for example cotton/polyester or cotton/polyamide/elastane or else nonwovens that are manufactured from cellulose or cellulose blend fabrics.

The problem addressed by the present invention was therefore that of overcoming at least one disadvantage of the prior art.

More particularly, the problem addressed was that of providing siloxanes/silicones having quaternary ammonium groups (called silicone quats) that have distinctly reduced proportions of unwanted organic by-products and/or low residual contents of unwanted organic reactants. More particularly, the problem addressed by the present invention was that of minimizing these unwanted organic compounds with simultaneous preparation of a hand-modifying active ingredient having higher efficacy on the textile.

It has been found that, surprisingly, specific siloxanes and specific compositions as described in the claims overcome at least one disadvantage of the prior art. More particularly, it has been found that these specific siloxanes and specific compositions lead to a better assessment of hand, better phase characteristics and a lower amide amine content.

These specific siloxanes bear at least two different quaternary ammonium groups, where at least one quaternary ammonium group is selected from the group consisting of quaternary amide ammonium groups and quaternary ester ammonium groups, preferably quaternary amide ammonium groups, and at least one quaternary ammonium group is selected from the group consisting of quaternary dialkanolammonium groups.

The specific compositions in turn contain these specific siloxanes.

The object of the present invention is therefore achieved by the subject-matter of the independent claims. Advantageous configurations of the invention are specified in the subsidiary claims, the examples and the description.

The inventive siloxanes, i.e. the inventive hand-modifying active ingredients, the inventive composition, the inventive process and the inventive use of the compositions and/or the process products are described by way of example hereinafter without any intention that the invention be restricted to these illustrative embodiments. Where ranges, general formulae or classes of compounds are specified hereinafter, these are intended to encompass not only the corresponding ranges or groups of compounds which are explicitly mentioned but also all subranges and subgroups of compounds which can be obtained by leaving out individual values (ranges) or compounds. Any embodiment that can be obtained by combination of regions/subregions and/or groups/subgroups, for example by combinations of essential, optional, preferred, preferable or preferably selected, further preferred, even further preferred, more preferred or especially preferred regions/subregions and/or groups/subgroups according to the invention is completely part of the disclosure-content of the present invention and is considered to be implicitly, directly and unambiguously disclosed. The expressions "with preference" and "preferably" are used synonymously.

Where documents are cited for the purposes of the present description, the entire content of these is intended to be part of the disclosure of the present invention.

Where content figures (ppm or %) are given hereinafter, unless stated otherwise, they are figures in % by weight or ppm by weight (ppmw). In the case of compositions, the content figures, unless stated otherwise, are based on the overall composition. Where average values are reported hereinafter, the values in question are numerical averages unless stated otherwise. Where molar masses are used, unless expressly noted otherwise, they are weight-average molar masses Mw. Where measurements or physical properties, for example surface tensions or the like, are reported hereinafter, unless stated otherwise, these are measurements or physical properties measured at 25° C. and preferably at a pressure of 101 325 Pa (standard pressure). Where values for viscosities are given within the scope of this invention, unless noted otherwise, these are dynamic viscosities that can be ascertained by the methods familiar to the person skilled in the art.

Where numerical ranges in the form of "from X to Y" are reported hereinafter, where X and Y are the limits of the numerical range, this is equivalent to the statement "from at least X up to and including Y", unless explicitly stated otherwise. Statements of ranges thus include the range limits X and Y, unless explicitly stated otherwise.

Wherever molecules/molecule fragments have one or more stereocenters or can be differentiated into isomers on account of symmetries or can be differentiated into isomers on account of other effects, e.g. restricted rotation, all possible isomers are embraced by the present invention.

In connection with this invention, the word fragment "poly" encompasses not just exclusively compounds having at least 2, especially 3, repeat units of one or more monomers in the molecule, but preferably also those compositions of compounds which have a molecular weight distribution and at the same time have an average molecular weight of at least 200 g/mol. This definition takes account of the fact that it is customary in the field of industry in question to refer to such compounds as polymers even if they do not appear to conform to a polymer definition as per OECD or REACH guidelines.

The various fragments in the formulae (I), (IV), (V) and (VI) below may be in a statistical distribution. Statistical distributions may have a blockwise structure with any number of blocks and any sequence or they may be subject to a randomized distribution; they may also have an alternating structure or else form a gradient along the chain, if there is one; in particular, they can also form any mixed forms thereof in which groups of different distributions may optionally follow one another. The indices a1, a2, a3, a4, b1, b2, b3, c1, c4, d, m, v, w, x, y, a5 and b5 used in the formulae are natural numbers. The alkyleneoxy units in formula (IV) may be bonded differently to the adjacent groups or atoms, meaning that, in formula (IV),

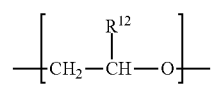

is in each case independently an alkyleneoxy radical of the $[CH_2CH(R^{12})O]$ form and/or of the $[CH(R^{12})CH_2O]$ form, but preferably an alkyleneoxy radical of the $[CH_2CH(R^{12})O]$ form. Specific executions may be defined hereinafter in that features such as indices or structural constituents or ranges or statistical distributions are subject to restrictions by virtue of the execution. All other features that are not affected by the restriction remain unchanged.

The present invention firstly provides a siloxane (A) of the formula (I)

$$M^1_{a1}M^2_{a2}M^3_{a3}M^4_{a4}D^1_{b1}D^2_{b2}D^3_{b3}T^1_{c1}T^4_{c4}Q_d \qquad \text{Formula(I)}$$

with
$M^1=[R^1_3SiO_{1/2}]$;
$M^2=[R^2R^1_2SiO_{1/2}]$;
$M^3=[R^3R^1_2SiO_{1/2}]$;
$M^4=[R^4R^1_2SiO_{1/2}]$;
$D^1=[R^1_2SiO_{2/2}]$;
$D^2=[R^1R^2SiO_{2/2}]$;
$D^3=[R^1R^3SiO_{3/2}]$;
$T^1=[R^1SiO_{3/2}]$;
$T^4=[R^4SiO_{3/2}]$;

Q=[SiO$_{4/2}$];
a1=0 to 32, preferably 0 to 19, especially 0 to 12;
a2=0 to 32, preferably 1 to 10, especially 1 to 3;
a3=0 to 32, preferably 1 to 10, especially 1 to 2;
a4=0 to 6, preferably 0 to 1, especially 0;
b1=1 to 1000, preferably 5 to 500, especially 10 to 400;
b2=0 to 10, preferably 0 to 5, especially 0;
b3=0 to 10, preferably 0 to 5, especially 0;
c1=0 to 10, preferably 0 to 5, especially 0 to 4;
c4=0 to 5, preferably 0 to 2, especially 0;
d=0 to 10, preferably 0 to 5, especially 0 to 4;
R$^1$=each independently identical or different hydrocarbon radicals, preferably having 1 to 30 carbon atoms,
  further preferably alkyl radicals having 1 to 30 carbon atoms or aromatic hydrocarbon radicals having 6 to 30 carbon atoms,
  even further preferably alkyl radicals having 1 to 14 carbon atoms or monocyclic aromatic hydrocarbon radicals.
  where the alkyl radicals are preferably linear or branched, saturated or unsaturated, even further preferably methyl, ethyl, propyl or phenyl, especially methyl;
R$^2$=R$^{21}$-R$^{22}$;
R$^{21}$=each independently identical or different divalent hydrocarbon radicals having at least one hydroxyl group and optionally further oxygen atoms and preferably 2 to 30 carbon atoms,
  further preferably additionally containing 1 to 2 further oxygen atoms, even further preferably containing functional groups selected from ether, carbonyl and ester groups,
  even further preferably each independently identical or different divalent radicals selected from the group consisting of

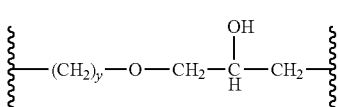

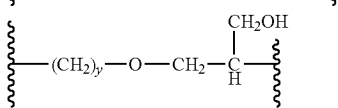

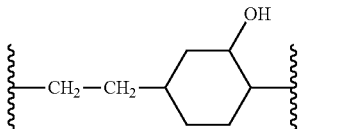

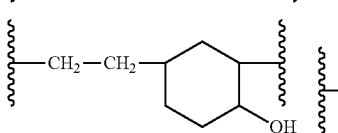

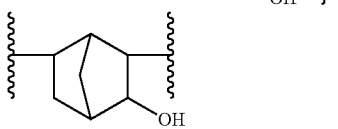

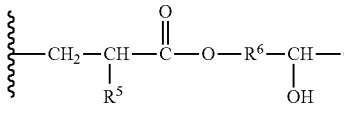

especially each independently identical or different divalent radicals selected from the group consisting of

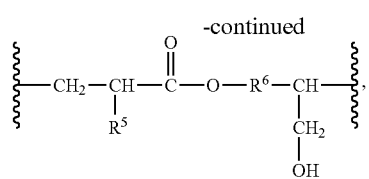

R$^{22}$=each independently identical or different radicals of the formula (II),

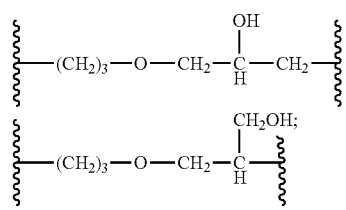

Formula (II)

R$^3$=R$^{31}$-R$^{32}$;
R$^{31}$=R$^{21}$;
R$^{32}$=each independently identical or different radicals of the formula (III)

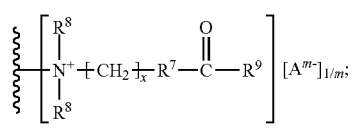

Formula (III)

R$^4$=each independently identical or different alkoxy groups or acyloxy groups, preferably having 1 to 6 carbon atoms,
  further preferably acetoxy groups and/or methoxy groups, ethoxy groups, n-propoxy groups, iso-propoxy groups, n-butoxy groups, tert-butoxy groups and/or alkoxy groups derived from glycol radicals, for example propylene glycol, dipropylene glycol, tripropylene glycol, hexylene glycol, pentylene glycol, butyldiglycol, especially isopropoxy groups;
R$^5$=each independently identical or different radicals selected from the group consisting of hydrogen and hydrocarbon radicals, preferably having 1 to 6 carbon atoms, further preferably selected from the group consisting of alkyl radicals having 1 to 6 carbon atoms, where the alkyl radicals are preferably linear or branched, saturated or unsaturated, especially methyl;
R$^6$=each independently identical or different divalent hydrocarbon radicals optionally containing ether groups, preferably having 1 to 6 carbon atoms, preferably methylene;

$R^7$=each independently identical or different divalent radicals selected from the group consisting of —O— and —NR$^{10}$—, preferably —NR$^{10}$—;

$R^8$=each independently identical or different radicals selected from the group consisting of hydrocarbon radicals preferably having 1 to 30 carbon atoms, further preferably selected from the group consisting of linear or branched, saturated or unsaturated alkyl radicals having 1 to 12 carbon atoms, even further preferably each independently identical or different radicals selected from the group consisting of methyl, ethyl, n-propyl, isopropyl, n-butyl, isobutyl, tert-butyl, even further preferably each independently identical or different radicals selected from the group consisting of methyl, ethyl, n-propyl, isopropyl, especially methyl;

$R^9$=each independently identical or different radicals selected from the group consisting of hydrogen and hydrocarbon radicals, preferably having 1 to 30 carbon atoms, further preferably selected from the group consisting of alkyl radicals having 1 to 30 carbon atoms, even further preferably alkyl radicals having 12 to 24 carbon atoms, especially having 16 to 22 carbon atoms, where the hydrocarbon radicals or alkyl radicals are preferably linear or branched, substituted or unsubstituted, saturated or unsaturated, more preferably linear, unsubstituted and saturated;

$R^{10}$=each independently identical or different radicals selected from the group consisting of hydrogen, —C(=O)R$^9$ and hydrocarbon radicals, preferably having 1 to 6 carbon atoms, further preferably alkyl radicals having 1 to 6 carbon atoms, where the hydrocarbon radicals or alkyl radicals are preferably linear or branched, substituted or unsubstituted, saturated or unsaturated, more preferably linear, unsubstituted and saturated; $R^{10}$ is especially preferably hydrogen;

$R^{11}$=each independently identical or different radicals selected from the group consisting of hydrocarbon radicals having at least one hydroxyl group and preferably 1 to 6 carbon atoms, preferably alkyl radicals having at least one hydroxyl group and preferably 1 to 6 carbon atoms, where the alkyl radicals are preferably linear or branched, saturated or unsaturated, and radicals of the formula (IV)

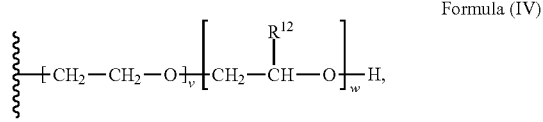

Formula (IV)

preferably 2-hydroxyethyl and/or 2-hydroxypropyl;

$R^{12}$=each independently identical or different radicals selected from the group consisting of hydrocarbon radicals, preferably having 1 to 6 carbon atoms, further preferably alkyl radicals having 1 to 6 carbon atoms, where the alkyl radicals are preferably linear or branched, saturated or unsaturated, preferably methyl and ethyl, especially methyl;

$A^{m-}$=each independently identical or different anions selected from inorganic or organic anions of the acids $H_mA$, and derivatives thereof;

m=1 to 3, preferably 1 to 2, especially 1;
v=0 to 30, preferably 0 to 10, especially 1 to 3;
w=0 to 30, preferably 0 to 10;
x=2 to 18, preferably 3;
y=2 to 18, preferably 3;
characterized in that conditions (i) and (ii) are applicable:

$$a2+b2 \geq 1; \qquad (i)$$

$$a3+b3 \geq 1. \qquad (ii)$$

The conditions (i) and (ii) ensure that the siloxane (A) has at least one amide ammonium group of formula (II) and at least one dialkanolammonium group of formula (III), i.e. at least one radical each of the following formulae (II) and (III):

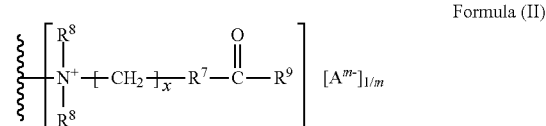

Formula (II)

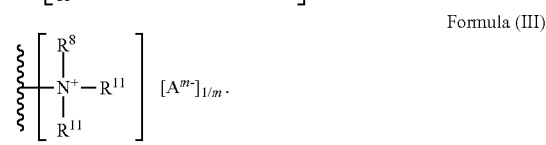

Formula (III)

The positive charges on the quaternary ammonium groups here are compensated for by a corresponding number of counterions $A^{m-}$.

A preferred siloxane (A) is a siloxane (A) of the formula (I)

$$M^1_{a1}M^2_{a2}M^3_{a3}M^4_{a4}D^1_{b1}D^2_{b2}D^3_{b3}T^1_{c1}T^4_{c4}Q_d \qquad \text{Formula (I)}$$

with
a1=0 to 32, preferably 0 to 19, especially 0 to 12;
a2=0 to 32, preferably 1 to 10, especially 1 to 3;
a3=0 to 32, preferably 1 to 10, especially 1 to 2;
a4=0 to 6, preferably 0 to 1, especially 0;
b1=1 to 1000, preferably 5 to 500, especially 10 to 400;
b2=0 to 10, preferably 0 to 5, especially 0;
b3=0 to 10, preferably 0 to 5, especially 0;
c1=0 to 10, preferably 0 to 5, especially 0 to 4;
c4=0 to 5, preferably 0 to 2, especially 0;
d=0 to 10, preferably 0 to 5, especially 0 to 4;

$R^1$=in each case independently identical or different hydrocarbon radicals having 1 to 30 carbon atoms, preferably selected from the group consisting of methyl, ethyl, propyl or phenyl, especially methyl;

$R^2$=$R^{21}$-$R^{22}$;

$R^{21}$=in each case independently identical or different divalent hydrocarbon radicals having at least one hydroxyl group and optionally 1 to 2 further oxygen atoms and 2 to 30 carbon atoms, preferably in each case independently identical or different divalent radicals selected from the group consisting of

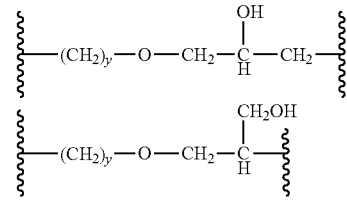

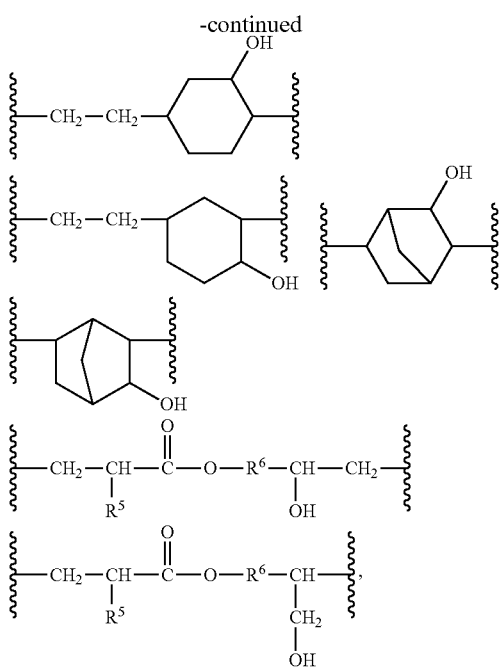

especially in each case independently identical or different divalent radicals selected from the group consisting of

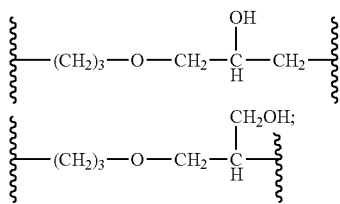

$R^{22}=$ in each case independently identical or different radicals of the formula (III)

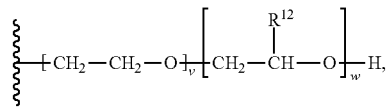

$R^3 = R^{31}\text{-}R^{32}$;
$R^{31} = R^{21}$;
$R^{32}=$ in each case independently identical or different radicals of the formula (III)

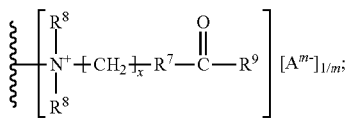

$R^4=$ in each case independently identical or different alkoxy groups or acyloxy groups having 1 to 6 carbon atoms, preferably acetoxy groups and/or methoxy, ethoxy, n-propoxy, isopropoxy, n-butoxy, tert-butoxy groups, especially isopropoxy groups;

$R^5=$ in each case independently identical or different radicals selected from the group consisting of hydrogen and hydrocarbon radicals having 1 to 6 carbon atoms, preferably selected from the group consisting of alkyl radicals having 1 to 6 carbon atoms, where the alkyl radicals are linear or branched, saturated or unsaturated, especially methyl;

$R^6=$ in each case independently identical or different divalent hydrocarbon radicals optionally containing ether groups and having 1 to 6 carbon atoms, preferably and especially methylene;

$R^7=$ in each case independently identical or different divalent radicals selected from the group consisting of —O— and —$NR^{10}$—, preferably and especially —$NR^{10}$—;

$R^8=$ in each case independently identical or different radicals selected from the group consisting of hydrocarbon radicals having 1 to 30 carbon atoms, preferably in each case independently identical or different radicals selected from the group consisting of methyl, ethyl, n-propyl, isopropyl, especially methyl;

$R^9=$ in each case independently identical or different radicals selected from the group consisting of hydrocarbon radicals having 1 to 30 carbon atoms, preferably in each case independently identical or different radicals selected from the group consisting of alkyl radicals having 12 to 24 carbon atoms, especially having 16 to 22 carbon atoms;

$R^{10}=$ in each case independently identical or different radicals from the group consisting of hydrogen, —C(=O)$R^9$ and hydrocarbon radicals having 1 to 6 carbon atoms, preferably selected from the group consisting of hydrogen and alkyl radicals having 1 to 6 carbon atoms, especially hydrogen;

$R^{11}=$ in each case independently identical or different radicals selected from the group consisting of hydrocarbon radicals having at least one hydroxyl group and 1 to 6 carbon atoms, and radicals of the formula (IV)

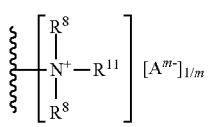

preferably and especially 2-hydroxyethyl and/or 2-hydroxypropyl;

$R^{12}=$ in each case independently identical or different radicals selected from the group consisting of hydrocarbon radicals having 1 to 6 carbon atoms, preferably methyl and ethyl, especially methyl;

$A^{m-}=$ in each case independently identical or different anions selected from inorganic or organic anions of the acids $H_mA$, and derivatives thereof;

m=1 to 3, preferably and especially 1 to 2;
v=0 to 30, preferably and especially 0 to 10;
w=0 to 30, preferably and especially 0 to 10;
x=2 to 18, preferably and especially 3;
y=2 to 18, preferably and especially 3;
characterized in that conditions (i) and (ii) are applicable:

$$a2+b2\geq1; \quad\quad (i)$$

$$a3+b3\geq1. \quad\quad (ii)$$

A further preferred siloxane (A) is a siloxane (A) of the formula (I)

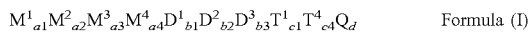 Formula (I)

with
a1=0 to 32, preferably 0 to 19, especially 0 to 12;
a2=0 to 32, preferably 1 to 10, especially 1 to 3;
a3=0 to 32, preferably 1 to 10, especially 1 to 2;
a4=0 to 6, preferably 0 to 1, especially 0;
b1=1 to 1000, preferably 5 to 500, especially 10 to 400;
b2=0 to 10, preferably 0 to 5, especially 0;
b3=0 to 10, preferably 0 to 5, especially 0;
c1=0 to 10, preferably 0 to 5, especially 0 to 4;
c4=0 to 5, preferably 0 to 2, especially 0;
d=0 to 10, preferably 0 to 5, especially 0 to 4;
$R^1$=in each case independently, identically or differently methyl, ethyl, propyl or phenyl, especially methyl;
$R^2=R^{21}-R^{22}$
$R^{21}$=in each case independently identical or different divalent radicals selected from the group consisting of

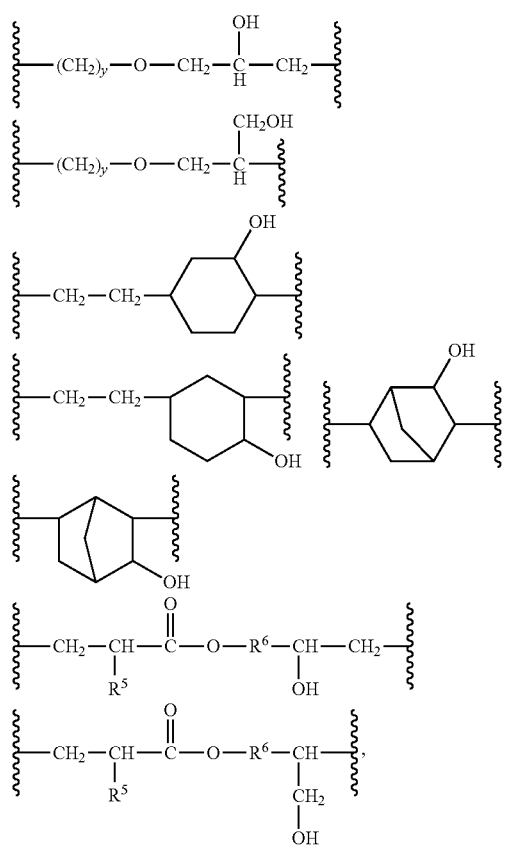

especially in each case independently identical or different divalent radicals selected from the group consisting of

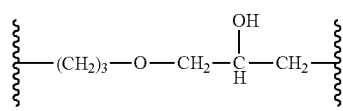

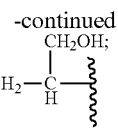

$R^{22}$=in each case independently identical or different radicals of the formula (II)

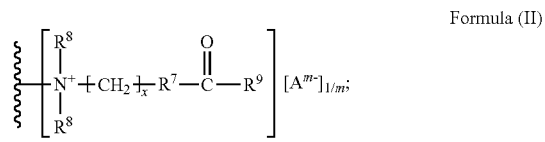 Formula (II)

$R^3=R^{31}-R^{32}$;
$R^{31}=R^{21}$;
$R^{32}$=in each case independently identical or different radicals of the formula (III)

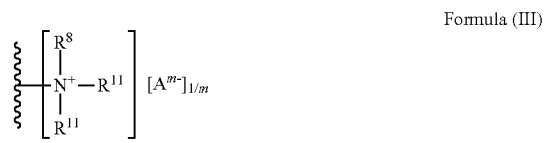 Formula (III)

$R^4$=in each case independently identical or different radicals selected from the group consisting of acetoxy, methoxy, ethoxy, n-propoxy, isopropoxy, n-butoxy and tert-butoxy, especially isopropoxy;
$R^5$=in each case independently identical or different radicals selected from hydrogen and methyl;
$R^6$=methylene;
$R^7$=in each case independently identical or different divalent radicals selected from the group consisting of —O— and —$NR^{10}$—, especially —$NR^{10}$—;
$R^8$=methyl;
$R^9$=in each case independently identical or different radicals selected from the group consisting of alkyl radicals having 12 to 24 carbon atoms, especially having 16 to 22 carbon atoms;
$R^{10}$=hydrogen;
$R^{11}$=in each case independently identical or different alkyl radicals having at least one hydroxyl group and 1 to 6 carbon atoms, especially 2-hydroxyethyl and/or 2-hydroxypropyl;
$R^{12}$=in each case independently identical or different alkyl radicals having 1 to 6 carbon atoms, especially methyl;
$A^{m-}$=in each case independently identical or different anions selected from inorganic or organic anions of the acids $H_mA$, and derivatives thereof;
m=1 to 3, preferably 1 to 2, especially 1;
v=0 to 30, preferably 0 to 10, especially 1 to 3;
w=0 to 30, preferably and especially 0 to 10;
x=2 to 18, preferably and especially 3;
y=2 to 18, preferably and especially 3;
characterized in that conditions (i) and (ii) are applicable:

$a2+b2\geq 1$;  (i)

$a3+b3\geq 1$.  (ii)

An even further preferred siloxane (A) is a siloxane (A) of the formula (I)

$$M^1{}_{a1}M^2{}_{a2}M^3{}_{a3}M^4{}_{a4}D^1{}_{b1}D^2{}_{b2}D^3{}_{b3}T^1{}_{c1}T^4{}_{c4}Q_d \quad \text{Formula (I)}$$

with
a1=0 to 32, preferably 0 to 19, especially 0 to 12;
a2=0 to 32, preferably 1 to 10, especially 1 to 3;
a3=0 to 32, preferably 1 to 10, especially 1 to 2;
a4=0 to 6, preferably 0 to 1, especially 0;
b1=1 to 1000, preferably 5 to 500, especially 10 to 400;
b2=0 to 10, preferably 0 to 5, especially 0;
b3=0 to 10, preferably 0 to 5, especially 0;
c1=0 to 10, preferably 0 to 5, especially 0 to 4;
c4=0 to 5, preferably 0 to 2, especially 0;
d=0 to 10, preferably 0 to 5, especially 0 to 4;
$R^1$=in each case independently, identically or differently methyl, ethyl, propyl or phenyl, especially methyl;
$R^2 = R^{21}\text{-}R^{22}$;
$R^{21}$=in each case independently identical or different divalent radicals selected from the group consisting of

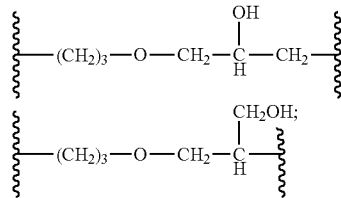

$R^{22}$=in each case independently identical or different radicals of the formula (II)

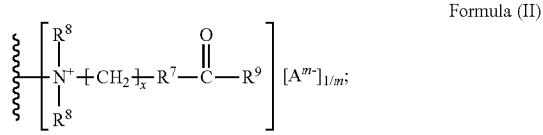

$R^3 = R^{31}\text{-}R^{32}$;
$R^{31} = R^{21}$;
$R^{32}$=in each case independently identical or different radicals of the formula (III)

$R^4$=in each case independently identical or different radicals selected from the group consisting of acetoxy, methoxy, ethoxy, n-propoxy, iso-propoxy, n-butoxy and tert-butoxy, especially iso-propoxy;
$R^7$=—NH—;
$R^8$=methyl;
$R^9$=in each case independently identical or different radicals selected from the group consisting of alkyl radicals having 16 to 22 carbon atoms;
$R^{11}$=in each case independently identical or different alkyl radicals having at least one hydroxyl group and 1 to 6 carbon atoms, especially 2-hydroxyethyl and/or 2-hydroxypropyl;

$A^{m-}$=in each case independently identical or different anions selected from inorganic or organic anions of the acids $H_mA$, and derivatives thereof;
m=1 to 3, preferably 1 to 2, especially 1;
x=2 to 18, preferably and especially 3;
characterized in that conditions (i) and (I) are applicable:

$$a2+b2 \geq 1; \quad \text{(i)}$$

$$a3+b3 \geq 1. \quad \text{(ii)}$$

In a preferred embodiment, the siloxane (A) is further characterized in that either condition (iii) or condition (iv) is additionally applicable:

$$a1=a4=b2=b3=c1=c4=d=0$$

and $$a2=a3=1; \quad \text{(iii)}$$

$$b2=b3=0$$

and $$c1+c4+d \geq 1$$

and $$a2+a3+a4 \geq 3, \text{ preferably } a2 \geq 2, a3 \geq 1 \text{ and } a4=0. \quad \text{(iv)}$$

A siloxane (A) that fulfils condition (iii) is a linear siloxane having no pendant siloxane groups, since it has no $T^1$, $T^4$ or Q units. Since the siloxane additionally does not have any $M^1$ unit or any $M^4$ unit, but has exactly one $M^2$ unit and exactly one $M^3$ unit, this unbranched siloxane has exactly one amide ammonium group of formula (II) at one of the two ends of the siloxane chain and exactly one dialkanolammonium group of formula (III) at the other of the two chain ends. Since said siloxane (A) additionally has neither $D^2$ nor $D^3$ units, the siloxane does not bear any pendantly bonded amide ammonium groups of formula (I) or dialkanolammonium groups of formula (I).

A siloxane (A) for which condition (iv) is applicable is in turn a branched siloxane since it has at least one unit selected from the group consisting of $T^1$, $T^4$ and Q units. This branched siloxane bears an amide ammonium group of formula (II) at at least one of its at least three ends and a dialkanolammonium group of formula (III) at at least one other end of its at least three ends. Since the siloxane additionally has neither $D^2$ nor $D^3$ units, amide ammonium groups of formula (II) or dialkanolammonium groups of formula (II) may be present only at the at least three ends of this branched siloxane. In addition, the siloxane may also bear one or more $R^4$ radicals, i.e. In each case independently identical or different alkoxy groups or acyloxy groups. If an $M^4$ unit is present, at least one $R^4$ radical is bonded to the ends of the branched siloxane. If a $T^4$ unit is present, at least one $R^4$ radical is bonded to a T branch site. Preferably, however, the siloxane for which condition (iv) is fulfilled does not have any $M^4$ units, i.e., preferably, a4=0. Further preferably, the siloxane for which condition (iv) is fulfilled also has exactly two $M^2$ units and exactly one $M^3$ unit. Thus, this siloxane bears an amide ammonium group of formula (II) at exactly two of its at least three ends and a dialkanolammonium group of formula (III) at exactly one of its at least three ends. It is especially preferable that there are no $T^4$ units; i.e., especially preferably, c4=0. The siloxane for which condition (iv) is fulfilled may also have $M^1$ units. However, it is preferable that there are no $M^1$ units; i.e., preferably, a1=0.

The invention further provides a composition comprising at least one siloxane (A).

The compositions according to the invention may, in preferred embodiments, contain either one or more siloxanes (A) to which condition (ii) is applicable or one or more siloxanes (A) to which condition (iv) is applicable, but they may also contain mixtures of these.

Preferably, the composition according to the invention further comprises at least one siloxane selected from the group consisting of siloxanes (B) and siloxanes (C).

Siloxane (B) is a siloxane that differs from a siloxane (A) at least in that, preferably precisely in that, the following conditions (v) and (vi) are applicable rather than the above-detailed conditions (i) to (v):

$$a2=b2=0, \quad (v)$$

$$a3+b3\geq 2. \quad (vi)$$

Siloxane (B) is thus a siloxane that differs from a siloxane (A) at least in that, preferably precisely in that, it has at least two dialkanolammonium groups of formula (III) and no amide ammonium groups of formula (II).

Siloxane (C) is a siloxane that differs from a siloxane (A) at least in that, preferably precisely in that, the following conditions (vii) and (viii) are applicable rather than the above-detailed conditions (i) and (iv):

$$a3=b3=0, \quad (vii)$$

$$a2+b2\geq 2. \quad (viii)$$

Siloxane (C) is thus a siloxane that differs from a siloxane (A) at least in that, preferably precisely in that, it has at least two amide ammonium groups of formula (II) and no dialkanolammonium groups of formula (III).

Thus, siloxanes (B) and (C) are also different from one another. Correspondingly, siloxanes (A), (B) and (C) are different from one another.

In a preferred embodiment, for the siloxane (A): $R^8$=methyl, x=3, $R^7$=—$NR^{10}$— with $R^{10}$=H.

In an alternative preferred embodiment, for the siloxane (A): $R^8$=methyl, $R^{11}$=—$CH_2CH_2OH$ and/or —$CH_2CH(CH_3)OH$.

In a particularly preferred embodiment, for the siloxane (A): $R^8$=methyl, x=3, $R^7$=—$NR^{10}$— with $R^{10}$=H, $R^{11}$=—$CH_2CH_2OH$ and/or —$CH_2CH(CH_3)OH$.

Further preferably, for the siloxane (B): $R^8$=methyl, $R^{11}$=—$CH_2CH_2OH$ or —$CH_2CH(CH_3)OH$.

Further preferably, for the siloxane (C): $R^3$=methyl, x=3, $R^7$=—$NR^{10}$— with $R^{10}$=H.

Especially preferably, $R^8$, x, $R^7$ and $R^{10}$ for siloxanes (A) and (B) and $R^8$ and $R^{11}$ for siloxanes (A) and (C) are the same.

Preferably, the proportion by mass of the at least one siloxane (A) based on the total mass of all siloxanes, more preferably based on the mass of siloxanes (A) and (B) and (C) together, is from 20% to 70%, preferably from 25% to 60%, especially from 30% to 50%.

In a preferred embodiment, the proportion by mass of the at least one siloxane (B) based on the total mass of the siloxanes, more preferably based on the mass of siloxanes (A) and (B) and (C) taken together, is from 0% to 15%, preferably from 1% to 10%.

Preferably, the proportion by mass of the at least one siloxane (C) based on the total mass of the siloxanes, more preferably based on the mass of siloxanes (A) and (B) and (C) taken together, is from 3% to 80%, preferably from 5% to 60%, especially from 10% to 50%.

By virtue of the preparation, it is possible that the composition according to the invention contains tertiary amines. However, it is preferable that the proportion of skin-Irritating, sensitizing and/or aquatoxic tertiary amines is low.

It is therefore further preferable that the proportion by mass of tertiary amines selected from the group of the ester amines and amide amines in the composition, based on the total mass of the siloxanes (A) and (B) and (C) taken together, totals less than 1% preferably less than 0.8%, further preferably less than 0.6%, even further preferably less than 0.4%, especially from 0% to 0.3%, or the composition does not contain any tertiary amines selected from the group of the amide amines.

An "amide amine" in the context of the present disclosure is understood to mean an N-alkylcarboxamide having at least one, preferably exactly one, tertiary amino group. An amide amine in the context of the present disclosure thus forms part of the group of the tertiary amines.

An "ester amine" in the context of the present disclosure is understood to mean an alkyl carboxylate having at least one, preferably exactly one, tertiary amino group. An ester amine in the context of the present disclosure thus forms part of the group of the tertiary amines.

A siloxane having quaternary ammonium groups in the context of the present disclosure is also referred to as "silicone quat" or as "quaternized siloxane".

It is further preferable that the proportion by mass of tertiary amines selected from the group consisting of dialkanolamines in the composition, based on the total mass of the siloxanes (A) and (B) and (C), is less than 3%, preferably less than 2%, further preferably less than 1%, especially from 0% to 0.5%, or the composition does not contain any tertiary amines selected from the group consisting of dialkanolamines.

A "dialkanolamine" in the context of the present disclosure is understood to mean a tertiary amine having a hydrocarbon radical and two hydroxy-functional alkyl radicals that are each bonded to the tertiary nitrogen atom. Preferably, the dialkanolamines are selected from alkyldialkanolamines (also referred to hereinafter as N-alkyldialkanolamines).

It is especially preferable that the proportion by mass of tertiary amines in the composition, based on the total mass of the siloxanes (A) and (B) and (C), is less than 3%, preferably less than 2%, further preferably less than 1%, especially from 0% to 0.5%, or the composition does not contain any tertiary amines.

It is further preferable that the proportion by mass of tertiary amines having a molecular weight of less than 500 g/mol in the composition, based on the total mass of the siloxanes (A) and (B) and (C), is less than 3%, preferably less than 2%, further preferably less than 1%, especially from 0% to 0.5%, or the composition does not contain any tertiary amines having a molecular weight of less than 500 g/mol.

It is preferable that the proportion by mass of tertiary amines selected from the group of the amide amines in the composition, based on the total mass of the siloxanes (A) and (B) and (C), totals less than 1%, preferably less than 0.8%, further preferably less than 0.6%, especially less than 0.4%, or the composition does not contain any tertiary amines selected from the group of the amide amines.

It is preferable that the proportion by mass of tertiary amines selected from the group of the ester amines in the composition, based on the total mass of the siloxanes (A) and (B) and (C), totals less than 1%, preferably less than 0.8%, further preferably less than 0.6%, especially less than 0.4%, or the composition does not contain any tertiary amines selected from the group of the ester amines.

In the context of the invention, preference is given to using amines that do not cause any damage to the skin or toxic effect via the skin and that are not harmful to the environment, especially not detrimental to sewage characteristics. Preferably, amines for which labelling is obligatory with one or more of the following H phrases according to the GHS classification should be avoided:

H310 Fatal in contact with skin
H311 Toxic in contact with skin
H312 Harmful in contact with skin
H314 Causes severe skin burns and eye damage
H315 Causes skin irritation
H317 May cause an allergic skin reaction
H400 Very toxic to aquatic life
H410 Very toxic to aquatic life with long-lasting effects
H411 Toxic to aquatic life with long-lasting effects
H412 Harmful to aquatic life with long-lasting effects
H413 May cause long-lasting harmful effects to aquatic life The preparation of silicones/siloxanes having quaternary ammonium groups (silicone quats) from epoxy-functional siloxanes and tertiary amines is known to those skilled in the art. Silicone quats can be prepared by the prior art processes as described, for example, in DE 3719086 C1, DE 3802622 A1 and DE 102010000993 A1.

Preferably, the siloxanes according to the invention are prepared by the process according to the invention, by reacting epoxy-functional siloxanes with mixtures of tertiary amines selected from the group consisting of amide amines and ester amines, preferably amide amines, and tertiary amines selected from the group consisting of dialkanolamines.

The present invention therefore further provides a process, preferably for preparing the siloxane (A) according to the invention and/or the composition according to the invention containing said siloxane (A), wherein the process includes at least one process step in which at least one epoxy-functional siloxane having at least two epoxy groups is reacted both with at least one tertiary amine selected from the group consisting of amide amines and ester amines, preferably amide amines, and with at least one tertiary amine selected from the group consisting of dialkanolamines to form quaternary ammonium groups.

Preferably, the tertiary amines selected from the group consisting of amide amines and ester amines are tertiary amines selected from the group consisting of amide amines. A process in which tertiary amines selected from the group consisting of amide amines are used is thus preferred over a process in which tertiary amines selected from the group consisting of ester amines are used.

Preferably, the conversion of the epoxy-functional siloxane affords those quaternary ammonium groups that result either from a reaction of the at least one tertiary amine selected from the group consisting of amide amines and ester amines, preferably amide amines, or from a reaction of the at least one tertiary amine selected from the group consisting of dialkanolamines with at least one of the at least two epoxy groups in each case in the epoxy-functional siloxane.

Preferably, epoxy groups are used in a molar excess, further preferably in equimolar amounts relative to tertiary amino groups, in order that the tertiary amines are converted to a maximum degree and their residual content after reaction is minimized, and further preferably the epoxysilanes are also additionally converted to a maximum degree and their residual content after reaction is minimized.

It is therefore preferable that the molar ratio of tertiary amino groups to epoxy groups is from 0.8:1 to 1:1, further preferably from 0.9:1 to 1, even further preferably from 0.95:1 to 1:1, even further preferably from 0.99:1 to 1:1, especially 1:1.

It is further preferable that the molar ratio ($mV_1$) of tertiary amino groups that are part of a tertiary amine selected from the group consisting of amide amines and ester amines, preferably amide amines, to epoxy groups is from 0.6:1 to 0.8:1, further preferably from 0.65:1 to 0.75:1, especially 0.7:1.

It is also preferable that the molar ratio ($mV_2$) of tertiary amino groups that are part of a tertiary amine selected from the group consisting of dialkanolamines to epoxy groups is from 0.4:1 to 0.2:1, further preferably from 0.35:1 to 0.25:1, especially 0.3:1.

The following condition preferably applicable here is $(mV_1)+(mV_2)=1:1$.

It is further preferable that the molar ratio of the at least one tertiary amine selected from the group consisting of amide amines and ester amines, preferably amide amines, to the at least one tertiary amine selected from the group consisting of dialkanolamines is from 90:10 to 60:40, preferably from 80:20 to 65:35, especially 70:30.

Especially preferably, the molar ratio of tertiary amines selected from the group consisting of amide amines to tertiary amines selected from the group consisting of alkyldialkanolamines is from 90:10 to 60:40, preferably from 80:20 to 65:35, especially 70:30.

As a result, the proportion of the quaternary ammonium groups that derive from a tertiary amine selected from the group consisting of dialkanolamines and the proportion of the quaternary ammonium groups that derive from tertiary amines selected from the group consisting of amide amines and ester amines, preferably amide amines, can be adjusted advantageously.

In a first embodiment of the process, the at least one epoxy-functional siloxane is reacted in a process step with at least one tertiary amine selected from the group consisting of dialkanolamines, and the reaction product obtained is reacted further in a process step that follows indirectly or directly with at least one tertiary amine selected from the group consisting of amide amines and ester amines, preferably amide amines.

In a second embodiment of the process, which is preferred over the first embodiment of the process, the at least one epoxy-functional siloxane is reacted in a process step with at least one tertiary amine selected from the group consisting of amide amines and ester amines, preferably amide amines, and the reaction product obtained is reacted further in a process step that follows indirectly or directly with at least one tertiary amine selected from the group consisting of dialkanolamines.

In a third embodiment of the process, which is preferred over the first and second embodiments of the process, the at least one epoxy-functional siloxane is reacted with a mixture of at least one tertiary amine selected from the group consisting of amide amines and ester amines, preferably amide amines, and at least one tertiary amine selected from the group consisting of dialkanolamines.

It is preferable when the reaction of the at least one epoxy-functional siloxane converts 90% to 100% of the epoxy groups, more preferably more than 92%. The % figures here indicate the number of epoxy groups converted divided by the number of epoxy groups used. The conversion of the epoxy groups, also referred to as epoxy conversion, can be determined with the aid of $^1$H NMR spectroscopy as described in the examples.

Preferably, the process products, after the reaction of the tertiary amines and the at least one epoxy-functional siloxane, are analysed for the absence of residual epoxy groups as described in the examples. If less than 90% of the epoxy groups have been converted, the reaction is conducted further until a conversion of 90% or more has been attained. Preferably, the batch is discarded if a conversion of 90% or more is not obtained.

For conversion of the tertiary amines, it is preferable to accelerate the reaction by catalysis. Catalysts used are preferably carboxylic acids, preferably acetic acid, isononanoic acid, lactic acid, especially acetic acid.

The catalyst is preferably used in a proportion by mass of 0.5% to 8%, preferably of 1% to 5%, based on the total mass of the reactants, i.e. neglecting further unreactive constituents, for example solvents.

The reaction of the epoxy-functional siloxane with the tertiary amines can be effected in the presence or absence, but preferably in the presence, of a solvent. Suitable organic solvents used are preferably anhydrous aliphatic alcohols, glycols or glycol ethers, for example methanol, ethanol, propanol, butanol, 2-propanol, tert-butanol, propylene glycol, dipropylene glycol, tripropylene glycol, hexylene glycol, pentylene glycol, buytyldiglycol, dipropylene glycol dimethyl ether, dipropylene glycol monomethyl ether, propylene glycol monomethyl ether, tripropylene glycol monomethyl ether, especially 2-propanol, dipropylene glycol, hexylene glycol.

Preferably, the reaction product obtained is purified by subjecting it to a suitable thermal separation process.

Thermal separation processes are known by this term to those skilled in the art and include all processes based on the establishment of a thermodynamic phase equilibrium. Preferred thermal separation processes are selected from the list comprising distillation, rectification, adsorption, crystallization, extraction, absorption, drying and freezing-out, particular preference being given to methods of distillation and rectification.

A preferred embodiment of the process therefore comprises, as a further process step, the distillation and/or purification of the reaction products. The distillation and/or purification can be effected, for example, by means of a rotary evaporator, preferably at a temperature of 20 to 250° C., more preferably 40 to 180° C. and more preferably 50 to 150° C., where the pressure is preferably from 0.0001 to 0.75 bar, even more preferably from 0.001 to 0.2 bar and more preferably from 0.01 to 0.1 bar. Distillation and/or purification is especially advantageous for removal of volatile constituents, especially of solvents.

Ester amines and/or amide amines used with preference are those of formula (VII)

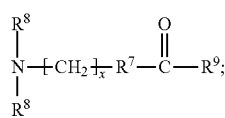

Formula (VII)

where $R^7$, $R^8$, $R^9$ and x are as defined in formula (II).

Particular preference is given to using amide amines of formula (VII).

The amide amines used in the process according to the invention are preferably reaction products from the reaction of dimethylaminoalkylamines, especially dimethylaminopropylamine (DMAPA), with fatty acids or fatty acid esters, for example the triglycerides of fatty acids. Particular preference is given to amide amines that derive from fatty acids having 10 to 30, further preferably 12 to 22, even further preferably 12 to 18, especially 16 to 18, carbon atoms.

Particular preference is therefore given to using amide amines of formula (VII) with $R^8$=methyl, x=3, $R^7$=—NR$^{10}$— with $R^{10}$=H.

Further preferably, $R^9$ is selected from the group consisting of alkyl radicals having 9 to 29, further preferably 11 to 21, even further preferably 11 to 17, especially 15 to 17, carbon atoms, where the alkyl radicals are unsubstituted or substituted by hydroxyl groups, linear or branched, saturated or unsaturated, preferably unsubstituted, linear and saturated.

Especially preferred are amide amines that are commercially available under the Tegoamid® trade name from Evonik, for example 3-N,N-dimethylaminopropylcocoamide (Tegoamid® D 5040 and Tegoamid® CNF), 3-N,N-dimethylaminopropylstearamide (Tegoamid® S 18) and 3-N,N-dimethylaminopropylpalmitamide (Tegoamid® PKFC).

Further suitable amide amines are disclosed in the publication *Safety Assessment of Fatty Acid Amidopropyl Dimethylamines as Used in Cosmetics, Final Repot*, Release Date: Jun. 24, 2014, Panel meeting Date: Jun. 9-10, 2014, *Cosmetic Ingredient Review* (https://www.cir-safety.org/sites/default/files/amidoa62014final.pdf), the explicit disclosure-content of which in this regard is incorporated into this disclosure by reference. Examples of these amide amines include:

almondamidopropyl dimethylamine
avocadamidopropyl dimethylamine
babassuamidopropyl dimethylamine
behenamidopropyl dimethylamine
brassicamidopropyl dimethylamine
cocamidopropyl dimethylamine
dilinoleamidopropyl dimethylamine
isostearamidopropyl dimethylamine
lauramidopropyl dimethylamine
linoleamidopropyl dimethylamine
minkamidopropyl dimethylamine
myristamidopropyl dimethylamine
oatamidopropyl dimethylamine
oleamidopropyl dimethylamine
olivamidopropyl dimethylamine
palmitamidopropyl dimethylamine
ricinoleamidopropyl dimethylamine
sesamidopropyl dimethylamine
soyamidopropyl dimethylamine
stearamidopropyl dimethylamine
sunlfowerseedamidopropyl dimethylamine
tallamidopropyl dimethylamine
tallowamidopropyl dimethylamine
wheat germamidopropyl dimethylamine Dialkanolamines used with preference are those of formula (VIII)

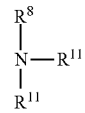

Formula (VIII)

where $R^8$ and $R^{11}$ are as defined in formula (III).

More preferably, the dialkanolamine is selected from the group consisting of N-methytldiethanolamine ($R^8$=—$CH_3$ and $R^{11}$=—$CH_2CH_2OH$), N-ethyldiethanolamine ($R^8$=—$CH_2CH_3$ and $R^{11}$=—$CH_2CH_2OH$), N-methyldiisopropanolamine ($R^8$=—$CH_3$ and $R^{11}$=—$CH_2CH(CH_3)OH$), N-ethyldiisopropanolamine ($R^8$=—$CH_2CH_3$ and $R^{11}$=—$CH_2CH(CH_3)OH$), N-isopropyidiaminoethanol ($R^8$=—$CH(CH)_2$ and $R^{11}$=—$CH_2CH_2OH$), N-butyldiethanolamine ($R^8$=—$CH_2CH_2CH_2CH_3$ and $R^{11}$=—$CH_2CH_2OH$), and the alkoxylation products thereof, where the alkoxylation products are preferably obtainable by reaction with ethylene oxide, propylene oxide, butylene oxide or mixtures of two or three of the alkylene oxides mentioned in a manner known to those skilled in the art.

Dialkanolamines used with especial preference are N-methyldiethanolamine ($R^8$=—$CH_3$ and $R^{11}$=—$CH_2CH_2OH$) and N-methyldiisopropanolamine ($R^8$=—$CH_3$ and $R^{11}$=—$CH_2CH(CH_3)OH$).

It has been found that, surprisingly, the reaction of epoxy-functional siloxanes with alkyldialkanolamines or the corresponding dialkylalkanolamines leads to a high conversion of epoxy groups, whereas the conversion of epoxy groups is only low or zero in a reaction with the corresponding trialkanolamines. In addition, it has been found that, surprisingly, the use of alkyldialkanolamines in a mixture with amide amines leads to a lower residual content of amide amines than the use of the corresponding dialkylalkanolamines in a mixture with amide amines. In addition, it is also surprising that alkyldialkanolamines are frequently less skin-irritating and/or sensitizing and/or aquatoxic than the corresponding dialkylalkanolamines.

In a preferred embodiment of the process, the residual content of tertiary amines selected from the group consisting of amide amines and ester amines, preferably amide amines, after the reaction, as a proportion by mass based on the total mass of the composition, is less than 1%, preferably less than 0.8%, further preferably less than 0.6%, especially less than 0.4%.

In a preferred embodiment of the process, the epoxy-functional siloxane is a siloxane of the formula (VI)

$$M^1{}_{a1}M^6{}_{a5}D^1{}_{b1}D^6{}_{b5}T^1{}_{c1}T^4{}_{c4}Q_d \qquad (VI)$$

with
$M^6=[R^{13}R^1{}_2SiO_{1/2}]$,
$D^6=[R^{13}R^1SiO_{2/2}]$,
$R^{13}$=each independently identical or different organic epoxy radicals, preferably selected from the group consisting of especially where
$M^1$, $D^1$, $T^1$, $T^4$, Q, a1, a5, b1, b5, c1, c4, d, $R^1$, R, $R^9$ and y are as defined in formula (I).

Preferably, the at least one epoxy-functional siloxane is prepared by hydrosilylation of at least one olefinically unsaturated epoxide.

Optionally, the at least one epoxy-functional siloxane, preferably the epoxy-functional siloxane of the formula (VI), prior to conversion thereof, is purified in that it is subjected to a suitable thermal separation process.

More preferably, the epoxy-functional siloxane is prepared by hydrosilylation of at least one olefinically unsaturated epoxide, preferably selected from the group consisting of allyl glycidyl ether, vinylcyclohexene monoxide and norbornadiene monoepoxide, especially allyl glycidyl ether, with at least one SiH-functional siloxane of the formula (V)

$$M^1{}_{a1}M^5{}_{a5}D^1{}_{b1}D^5{}_{b5}T^1{}_{c1}T^4{}_{c4}Q_d \qquad (V)$$

with
$M^5=[R^1{}_2SiHO_{1/2}]$.
$D^5=[R^1SiHO_{2/2}]$,
a5=0 to 32, preferably 1 to 10, more preferably 2 to 3, especially 2;
b5=0 to 10, preferably 0 to 5, especially 0;
where
$M^1$, $D^1$, $T^1$, $T^4$, Q, a, b1, c1, c4, d and $R^1$ are as defined in formula (I).

The hydrosilylation is effected in the manner known to those skilled in the art.

The hydrosilylation in the process according to the invention is preferably catalysed with the aid of the platinum group catalysts familiar to those skilled in the art, more preferably with the aid of Karstedt catalysts.

The hydrosilylation can be effected in the presence or absence, but preferably in the presence, of a solvent. Suitable organic solvents used are preferably toluene, xylene or isopropanol. The solvents used are preferably anhydrous. If the solvent has a reactive group, especially a hydroxyl group, this can lead to SiOC by-products to a minor degree.

It is preferable when the hydrosilylation converts more than 95%, further preferably more than 97%, especially 99% to 100%, of the SiH groups. The % figures indicate the number of SiH groups converted divided by the number of SiH groups used. The SiH groups are detected in a manner familiar to those skilled in the art, preferably by gas-volumetric means after alkaline breakdown.

This can be done, for example, by reacting a sample of the reaction mixture with a butanolic sodium butoxide solution (sodium butoxide content=5% by weight) and concluding the amount of SiH functions still present from the amount of hydrogen formed.

Optionally, the at least one SiH-functional siloxane of formula (V), prior to the hydrosilylation, is purified in that it is subjected to a suitable thermal separation process.

Likewise optionally, the epoxy-functional siloxane obtained is purified, preferably by means of a thermal separation process as described above.

The SiH-functional siloxanes can likewise be obtained by known methods via equilibration. The preparation of linear SiH-functional siloxanes by means of equilibration with trifluoromethanesulfonic acid is described, for example, in U.S. Pat. No. 5,578,892 or EP 2176319 B1.

By virtue of the preparation, it is possible that the process products contain the cyclic siloxanes octamethylcyclotetrasiloxane and decamethylcyclopentasiloxane. Octamethylcyclotetrasiloxane and decamethylcyclopentasiloxane are non-biodegradable. Octamethylcyclotetrasiloxane is additionally of toxicological concern. For these reasons, it is advantageous that the molar proportion of decamethylcyclopentasiloxane and/or octamethylcyclotetrasiloxane is at a minimum.

In a preferred embodiment of the composition according to the invention and the process product according to the invention, the proportion by mass of decamethylcyclopentasiloxane, based on the overall composition according to the invention or the overall process product according to the invention, is less than 1% and is especially preferably from 0% to 0.1%.

In a preferred embodiment of the composition according to the invention and the process product according to the invention, the proportion by mass of octamethylcyclotetrasiloxane, based on the overall composition according to the invention or the overall process product according to the invention, is less than 1% and is especially preferably from 0% to 0.1%.

The process according to the invention can preferably be executed in such a way that there are two process steps: 1. preparation of an epoxy-functional siloxane, and 2. reaction of the epoxy-functional siloxane with a tertiary amine selected from the group consisting of amide amines and ester amines, preferably amide amines, and a tertiary amine selected from the group consisting of dialkanolamines to give the quaternized silicones according to the invention. The process steps of the aforementioned preferred embodiment of the invention can be conducted in the process according to the invention as successive steps conducted separately, each in the form of a one-pot reaction or else under metering control, but preferably under metering control. The reaction can be conducted in a batchwise, semi-batchwise or continuous process. Metering-controlled reaction is especially preferred in process steps 1 and 2.

The process according to the invention can be effected in the presence or in the absence of a solvent. Suitable organic solvents used for the 1st process step are preferably toluene, xylene or 2-propanol. Suitable organic solvents used for the 2nd process step are preferably anhydrous aliphatic alcohols, glycols or glycol ethers, for example methanol, ethanol, propanol, butanol, 2-propanol, tert-butanol, propylene glycol, dipropylene glycol, tripropylene glycol, hexylene glycol, pentylene glycol, butyldiglycol, dipropylene glycol dimethyl ether, dipropylene glycol monomethyl ether, propylene glycol monomethyl ether, tripropylene glycol monomethyl ether, especially 2-propanol, dipropylene glycol, hexylene glycol.

If the solvent has a reactive group, especially a hydroxyl group, it can lead to SiOC by-products to a minor degree. The hydroxyl groups in the dialkanolamines used can likewise form traces of SiOC by-products.

The reactants may be present here in any desired concentration in a solvent, for example 5% to 99% by weight, preferably 80% to 95% by weight, especially preferably 85% to 95% by weight, based on the overall composition.

In a preferred embodiment, the process according to the invention can be conducted at a temperature of 10° C. to 150° C., preferably of 25° C. to 100° C., more preferably of 40° C. to 90° C.

In a preferred embodiment, the process according to the invention can preferably be conducted at a pressure of 0.5 to 20 bar, preferably 1 to 5 bar, especially preferably at standard pressure.

The reaction according to the invention can be conducted either in daylight or with exclusion of light, preferably in daylight.

The reaction according to the invention can be conducted either under inert conditions (nitrogen, argon) or under an oxygen and/or air atmosphere, preferably under a nitrogen atmosphere.

The invention further provides a composition that can be obtained by the process according to the invention.

In a preferred embodiment, the composition according to the invention comprises water as a further constituent.

The composition is preferably an aqueous emulsion.

It is further preferable that the composition, preferably the aqueous emulsion, contains the following components in parts by mass based on the total mass of the composition:
a) 20% to 99.5%, preferably 40% to 97%, especially 60% to 95%, water;
b) 0.5% to 80%, preferably 3% to 60%, especially 5% to 40%, of at least one siloxane comprising at least one siloxane (A) and preferably at least one siloxane (B) and/or at least one siloxane (C);
c) preferably 1% to 10% of at least one emulsifier;
d) preferably 5% to 20% of at least one glycol; and
e) preferably 0% to 1% acetic acid.

The compositions according to the invention, especially the aqueous emulsions, preferably further comprise additives which may be selected from the group consisting of boosters, emulsifiers, solvents, perfume, perfume carriers, dyes, viscosity regulators, defoamers, preservatives, active antimicrobial ingredients, germicides, fungicides, antioxidants, organic solvents, non-siloxane-containing polymers and other non-inventive siloxane-containing polymers, for example non-inventive siloxane-containing silicone oils, surfactants, builders, bleaches, bleach activators, enzymes, fluorescers, foam inhibitors, antiredeposition agents, optical brighteners, greying inhibitors, antishrink agents, anticrease agents, dye transfer inhibitors, corrosion inhibitors, non-Inventive antistats, bitter substances, ironing aids, repellency-imparting and impregnating agents, antiswell and antislip agents, neutral filler salts and UV absorbers. It is possible here for substances from one class also to display efficacy in another class.

More particularly, the compositions according to the invention may contain between 0.001% and 40% by weight, more preferably 0.01% to 20% by weight, of one or more different additives or auxiliaries, based on the total mass of the siloxanes (A) and (B) and (C) or the process products according to the invention.

Preferably, the compositions according to the invention are in the form of concentrates, compounds/emulsion concentrates and/or the aqueous formulations thereof, of aqueous emulsions and/or solutions, and/or of a formulation or emulsion in organic compounds such as polyethers, polyols, alcohols.

Additionally particularly preferred compositions according to the invention are concentrates containing the siloxanes according to the invention or the process products according to the invention in a concentration of 75% to 99.99% by weight, based on the overall composition. Thus, only small proportions of solvents have been added to these concentrates. The concentrates are preferably not aqueous solutions.

Further particularly preferred compositions according to the invention are compound or emulsion concentrates containing the siloxanes according to the invention or the process products according to the invention in concentrations of 40% to 90% by weight, preferably 50% to 80% by weight, based on the overall mass. Further constituents of these compound or emulsion concentrates are water and/or solvents selected from the group of the glycols, unbranched and/or branched alcohols and/or alkyl ethers having 1 to 6 carbon atoms and optionally one or more nonionic emulsifiers, for example an alcohol ethoxylate having 3 to 25 ethylene oxide units. Compound and emulsion concentrates are generally water-soluble or self-emulsifiable.

Particularly preferred aqueous emulsions according to the invention, preferably microemulsions, are hand modifiers for treatment of textile fabrics.

Fabrics in the context of this invention are solid or composed of fibres, such as wood, cotton, polyester, polyamide, synthetic fibres, paper and cardboard, viscose, cellulose and/or lignin-based fibres. Fabrics in the context of this invention likewise include hard surfaces of metal, ceramic, glass, wood or plastic.

Preferred fabrics are selected from the group comprising woven textile fabrics, hair and fur, preference being given especially to woven textile fabrics, loop-formed knits, loop-drawn knits, nonwovens, tissue (paper fibres) and/or other fibres made from natural and/or synthetic raw materials.

Especially preferred compositions according to the invention are hand modifiers for temporary or permanent finishing of textiles.

The compositions according to the invention may optionally comprise further non-inventive textile softeners. These are one or more cationic textile-softening compounds having one or more long-chain alkyl groups in one molecule. Widely used cationic textile-softening compounds include, for example, alkanolamine-ester quat compounds or known quaternary ammonium compounds, esterified with two C18-acyl groups. Further suitable ammonium compounds are disclosed in US 2010/0184834 in paragraphs [0027] to [0068], the explicit disclosure content of which in this regard is incorporated into this disclosure by this reference.

By dilution with water, it is possible to use the concentrates, emulsion concentrates and formulations according to the invention, for example, to produce the finishing agents according to the invention for textiles.

The aqueous emulsions according to the invention as hand modifiers for textile fabrics contain the siloxanes according to the invention or the process products according to the invention in a proportion by mass of 3% to 35%, preferably of 5% to 25%, especially of 7% to 20%, based on the overall composition.

Emulsifiers used are typically fatty alcohol ethoxylates having ethoxylation levels between 3 and 12, specifically in a mass ratio of the siloxanes (A), (B) and (C) together to the fatty alcohol ethoxylates of 20:1 to 1:1. High-boiling glycols such as dipropylene glycol or butyldiglycol are likewise typically employed. These glycols may entirely or partly replace the fatty alcohol ethoxylates.

Preferably, emulsifiers are present in the compositions according to the invention and the aqueous emulsions according to the invention in a proportion by mass of 1% to 10%, more preferably of 1.5% to 8%, based on the overall composition.

Defoamers used may be any defoamers known to be suitable for aqueous textile liquors from the prior art. Examples of suitable commercial defoamers are available under the Dow Corning® DB-110A and TEGO® Antifoam® MR 1015 name.

Preferably, the composition according to the invention contains at least one defoamer in a proportion by mass of 0.0001% to 0.05%, more preferably of 0.001% to 0.01%, based on the overall composition.

As preservative, the composition may comprise active bactericidal and/or fungicidal ingredients known to be suitable from the prior art, preference being given to water-soluble active ingredients. Examples of suitable commercial bactericides are methylparaben, 2-bromo-2-nitropropane-1,3-diol, 2-methyl-4-Isothiazolin-3-one and 5-chloro-2-methyl-4-isothiazolin-3-one.

The composition according to the invention may likewise contain a preservative, preferably an oxidation inhibitor. Examples of suitable commercial oxidation inhibitors are ascorbic acid, 2,8-di-tert-butyl-4-methylphenol (BHT), butylhydroxyanisole (BHA), tocopherol and propyl gallate. Preferably, the compositions according to the invention contain at least one preservative in a proportion by mass of 0.0001% to 0.5%, more preferably of 0.001% to 0.2%, based on the overall composition. In particular, the compositions may contain at least one oxidation inhibitor in a proportion by mass of 0.001% to 0.1%, more preferably of 0.001% to 0.01%, based on the overall composition.

As organic solvent, the composition may comprise short-chain alcohols, glycols and glycol monoethers, preference being given to ethanol, 2-propanol, propane-1,2-diol and dipropylene glycol. In particular, the compositions according to the invention may contain at least one organic solvent in a proportion by mass of 0.1% to 10%, more preferably of 0.2% to 5%, based on the overall composition.

The invention further provides for the use of the siloxanes and/or compositions and/or process products according to the invention a) for treatment, preferably finishing and/or impregnation, of two-dimensional structures;

b) in cleaning and care formulations for the household and for industrial purposes, especially in fabric softeners;

c) in cosmetic, pharmaceutical and dermatological compositions, especially in cosmetic cleansing and care formulations, hair treatment products and hair after-treatment products; and/or d) for cleaning and care of hard surfaces, preferably for cleaning and care of motor vehicles, especially as additive in drying aids for carwash facilities.

Preference is given to the use of the siloxanes and/or compositions and/or process products according to the invention for finishing of textile fabrics.

More preferred is the use of the siloxanes and/or compositions and/or process products according to the invention in hydrophilic hand-modifying compositions, especially in textile-softening compositions (fabric softeners).

Further preferably, the siloxanes, compositions and/or process products according to the invention are used as softeners for fabrics.

They are used, for example, in fabric softener compositions, especially aqueous fabric softener compositions. Aqueous fabric softener compositions are typically added to the last wash cycle in the washing of laundry in a washing machine in order to give a softer hand to the laundry. Fabric softener compositions of this kind contain the siloxanes according to the invention in an amount of 2% to 20% by weight, based on the fabric softener composition, dispersed in an aqueous solution.

For use as a softener for fabrics, the siloxanes according to the invention have a molar ratio of silicon atoms to quaternary ammonium groups of more than 25:1, preferably of 50:1 to 200:1.

Silicone quats are used not just to improve hand in textile processes, but also as antistats with friction-reducing action.

Further preferably, the siloxanes, according to the invention, the compositions according to the invention and the process products according to the invention are therefore used as antistats.

Further preferably, the siloxanes according to the invention, the compositions according to the invention and the process products according to the invention are used as glidants. Thus, they preferably have a friction-reducing effect.

Suitable siloxanes for use as antistats and/or as glidants are especially those that have a low molecular weight based on the number of quaternary ammonium groups.

Preferably, the siloxanes according to the invention, for use as antistats, therefore have fewer than 50 silicon atoms, especially 15 to 30 silicon atoms.

For use as antistats or for use for treatment of hard surfaces, especially in the automotive sector, the siloxanes according to the invention have a molar ratio of silicon atoms to quaternary ammonium groups of less than 25:1, preferably of 5:1 to 25:1, especially 10:1 to 15:1.

Further preferably, the siloxanes, compositions and/or process products according to the invention are used as cleaning and care compositions for hard surfaces, preferably for cleaning and care of motor vehicles, especially as additive in drying aids for carwash facilities.

The cleaning and care of hard surfaces, especially the washing of motor vehicles in carwash facilities, can be divided into a prewash and main wash. It is possible here to use different compositions. The cleaning removes soil particles on the surface of the vehicle. This cleaning is followed by the rinsing operation in which cleaning composition residues are removed. This step serves for preparation for the use of a drying agent that hydrophobizes the vehicle prior to the final blow-drying, and the remaining film of water can thus be removed more easily. The rinsing operation is advantageous because drying agents are of cationic character and can otherwise, after the application of anionic cleaning formulations, form sparingly soluble salts that lead to spots on the vehicle and hence lead neither to the desired gloss effect nor to hydrophobization. In applications where the surface-active compound is required to remain on the material treated, the silicone quats according to the invention form the essential constituents of these formulations. The silicone quats according to the invention are being widely used in applications in the field of fabric softeners, textile finishing or hair rinses, and also in dryer applications in carwash facilities. Since even vehicle paints, like most surfaces, have a negative electrical surface potential, the silicone quats spread out on the vehicle after the drying agent formulation has been sprayed on and displace the film of water present. The silicone quats lead to an enhancement of the colour impression and gloss impression of the paint and give protection from weathering effects.

The siloxanes according to the invention and/or the composition according to the invention and/or the process products according to the invention have numerous advantages over prior art silicone quats; more particularly, they exhibit:

a) a greater effect at the same use concentration;
b) reduced proportions of unwanted organic compounds, especially organic compounds of low molecular weight, and hence a significant reduction in the risk potential of a skin-sensitizing effect or harm to water bodies when introduced into surface water which is associated with these compounds;
c) better processability and lower viscosity with the same amount of active ingredient and simultaneously a smaller use of solvents or emulsifiers;
d) longer shelf life;
e) lower penetration tendency of the finishing agent;
f) unchanged breathability of the textiles finished therewith;
g) a high level of effect of the textiles finished therewith even after multiple washes;
h) improvement in the tactile properties and more pleasant wear comfort of the textiles finished therewith; and/or
i) good storage stability, meaning that the viscosity is stable in storage and the new formation of cyclic siloxanes is minimized; and/or
j) Improved pH stability up to a pH of 11.

EXAMPLES

General Methods
Nuclear Spin Resonance Spectroscopy (NMR Spectroscopy)

The siloxanes can be characterized with the aid of $^1$H NMR and $^{29}$Si NMR spectroscopy. These methods, especially taking account of the multiplicity of the couplings, are familiar to the person skilled in the art.

The conversion of the epoxy groups (epoxy conversion) can be determined with the aid of $^1$H NMR spectroscopy.
Gel Permeation Chromatography (GPC):

GPC measurements for determination of the polydispersity and weight-average molar masses Mw are conducted under the following measurement conditions: Column combination SDV 1000/10 000 Å (length 55 cm), temperature 35° C., THF as mobile phase, flow rate 0.35 ml/min, sample concentration 10 g/l, RI detector, evaluation of the polymers against polystyrene standard (162 2 520 000 g/mol).
High-performance liquid Chromatography (HPLC):

To determine the concentration of amide amines (Tegoamid® S18, Tegoamid® D5040, Tegoamid® PKFC), reverse-phase HPLC is conducted with gradient conditions. An RP-C18 column (Inertsil ODS-3, GL Science) is used as stationary phase. Acetonitrile and dilute sulfuric acid are employed as binary eluent system. Detection is effected by UV detector at a wavelength of 210 nm. The external standard used for the calibration is specific amide amines that are used in the respective synthesis of the siloxane/silicone quat. The residual content is reported in percent by weight based on the corresponding composition.
Gas Chromatography:

The proportion by mass of cyclic siloxanes, especially octamethylcyclotetrasiloxane (D4) and decamethylcyclopentasiloxane (D5), can be determined with the aid of a gas chromatography method (GC method) in which the substances are separated according to their boiling point and detected by means of a thermal conductivity detector. This is done by analysing an aliquot of the sample to be examined without further dilution by means of GC. This is conducted in a gas chromatograph equipped with a spilt/splitless injector, a capillary column and a thermal conductivity detector, under the following conditions:

Injector: 290° C., split 40 ml
Injection volume: 1 μl
Column: 5 m*0.32 mm HP5 1 μm
Carrier gas: helium, const. flow, 2 ml/min Temperature program: 1 minute at 80° C., then 80° C.-300° C. at 30° C./min, then conditioning at 300° C. for 10 minutes.
Detector: TCD at 320° C.
Make-up gas 6 m/min
Reference gas 18 ml/min The cyclic siloxanes are separated according to their boiling point. The proportion by mass of the individual substances is determined as the percentage of the peak areas determined for the respective substance by comparison with the total area of all substances detected (area % method).

Viscosity:

Viscosity is measured with a Brookfield R/S-CPS Plus rheometer using the RP75 measurement plate at 25° C. The test method is described in DIN 53019 (DIN 53019-1: 12008-09, DIN 53019-2:2001-02 and DIN 53019-3:2008-09).

General Synthesis Method:

The quaternized siloxanes (also referred to here as active ingredients or silicone quats) are prepared in the manner known to the person skilled in the art, as described in the prior art, for example in publications DE 102010000993 A1 and DE 3802622 A1. The preparation is effected in three stages. In the first stage the SiH-functional siloxanes are prepared. In the second stage the SiH-functional siloxanes prepared are used to prepare epoxy-functional siloxanes by means of hydrosilylation. In the third stage the epoxy-functional siloxanes obtained are reacted with tertiary amines under acid catalysis as follows:

1st Stage—Preparation of SiH-Functional Siloxanes:
Linear Terminal SiH Siloxanes:

An inertized 500 ml three-neck flask with a precision glass stirrer, reflux condenser and internal thermometer was initially charged with the respective amounts (cf. Table 1) of decamethylcyclopentasiloxane (D5) and α,ω-dihydropolydimethylsiloxane (α,ω-dihydro-PDMS) having an SiH value of 2.97 mmol/g, and 0.25 g of trifluoromethanesulfonic acid was added while stirring. After stirring at 40° C. for 6 h, 5 g of sodium hydrogencarbonate were added and the mixture was stirred for 2 h. After filtration, transparent, fluid, colourless products were obtained.

Starting weights and further details of the preparation of the SiH-functional siloxanes can be found in Table 1.

TABLE 1

Starting weights and further details of the preparation of the SiH-functional siloxanes of formula (V)

| SiH siloxane | a5 | b1 | $R^1$ | α,ω-dihydro-PDMS | D5 |
|---|---|---|---|---|---|
| SH1 | 2 | 48 | methyl | 45.5 g | 204.5 g |
| SH2 | 2 | 78 | methyl | 28.5 g | 221.5 g |
| SH4 | 2 | 18 | methyl | 114.6 g | 135.4 g |
| SH5 | 2 | 28 | methyl | 76.2 g | 173.8 g |

Branched SiH Siloxane (SH3):

The preparation was effected as disclosed in document EP 2176319 B1.

44.2 g (0.248 mol) of methyltriethoxysilane, 125.3 g of an α,ω-dihydropolydimethylsiloxane having a hydrogen content of 2.97 mmol SiH/g and 1352.5 g of decamethylcyclopentasiloxane were initially charged in a four-neck flask equipped with a precision glass stirrer, an internal thermometer, a dropping funnel and a distillation system while stirring at room temperature, 1.5 g of trifluoromethanesulfonic acid were added and the mixture was stirred for 30 minutes. A mixture of 13.4 g of deionized water and 20 ml of methanol was added dropwise while stirring within a further 30 minutes, and the mixture was stirred for a further 30 minutes. The reaction mixture was heated to 40° C. for 1 hour and then distilled in a waterjet-pump vacuum of about 50 mbar at 40° C. for 1 hour. After neutralization with 30.4 g of sodium hydrogencarbonate and filtration, 152 g of Lewatit® K 2821, a predried sulfonic acid cation exchange resin, were added, and the mixture was stirred at 40° C. for 4 hours and filtered. This gave a clear, colourless liquid.

2nd Stage—Preparation of Epoxy-Functional Siloxanes:

An inertized 500 ml three-neck flask with precision glass stirrer, Internal thermometer and reflux condenser was initially charged with the respective amounts of SiH siloxane and allyl glycidyl ether (AGE) (cf. Table 2) and heated up to 70° C. while stirring. 0.13 g of Karstedt catalyst (0.1% Pt) was added with a syringe and the mixture was stirred at 80° C. for a further 2 h, if required with counter-cooling of the initial exothermicity. After distillation at 120° C. and 1 mbar for 3 h, a transparent, pale beige, fluid product of viscosity 135 mPa*s was obtained. The hydrosilylation reaction was brought to full conversion in relation to the hydrogen content of the SiH-functional siloxanes. In the context of the present invention, full conversion is understood to mean that more than 99% of the SiH functions were converted. Detection is effected in a manner familiar to the person skilled in the art by gas-volumetric means after alkaline breakdown.

Starting weights and further details of the preparation of the epoxy-functional siloxanes can be found in Table 2.

TABLE 2

Starting weights and further details of the preparation of the epoxy-functional siloxanes of formula (VI)

| Epoxysiloxane | a5 | b1 | c1 | $R^1$ | SiH siloxane | AGE |
|---|---|---|---|---|---|---|
| SE1 | 2 | 48 | 0 | methyl | 231.4 g SH1 | 18.6 g |
| SE2 | 2 | 78 | 0 | methyl | 238.1 g SH2 | 11.9 g |
| SE3 | 6 | 316 | 4 | methyl | 241.1 g SH3 | 8.9 g |
| SE4 | 2 | 18 | 0 | methyl | 208.0 g SH4 | 42.0 g |
| SE5 | 2 | 28 | 0 | methyl | 220.4 g SH5 | 29.6 g |

3rd Stage—Preparation of the Silicone Quats:

An inertized 500 ml three-neck flask with precision glass stirrer, dropping funnel, Internal thermometer and reflux condenser was initially charged with the respective amounts (cf. Table 3) of amide amine, alkanolamine and solvent, the respective amount of carboxylic acid was metered in and the mixture was stirred at room temperature for 1 hour. Subsequently, the respective epoxy-functional siloxane was added dropwise, and the mixture was heated to 80° C. and stirred for 12 to 16 hours until a conversion of epoxy groups (also referred to as epoxy conversion) of at least 90% had been attained. The conversion of the epoxy groups was determined by NMR spectroscopy. Optionally, the solvent was removed by distillation and exchanged by subsequent blending with another solvent, i.e. by dilution of the distillation residue obtained with another solvent.

The following raw materials were used in the preparation of the silicone quats:

Amide1=3-N,N-dimethylaminopropylcocoamide, Tegoamid® D 5040, Evonik

Amide2=3-N,N-dimethylaminopropylstearamide, Tegoamid® S 18, Evonik

Amide3=3-N,N-dimethylaminopropylpalmitamide, Tegoamid® PKFC, Evonik

MDEA=N-methyldiethanolamine, 99%, Sigma-Aldrich

MDIPA=N-methyldiisopropanolamine, BASF
TEA=triethanolamine, 99%. Sigma-Aldrich
DMAE=dimethylglycine (dimethylaminoacetic acid), >98%. Alfa-Aesar
HOAc=acetic acid, p. A. Baker
INA=isononanoic acid, 97%, Alfa-Aesar
IPA=isopropanol, >99.9%, Sasol
tBuOH=tert-butanol, ACS, Reag. Ph Eur, Merck
DPG=dipropylene glycol, >=99%, Lyondell
PG=1,2-propylene glycol, >=99%, Lyondell
DMM=dipropylene glycol dimethyl ether, >94%, TCI Europe N.

Amide1 is prepared here by reaction of hydrogenated coconut fat with 3-aminopropyldiethylamine (DMAPA). The reaction leads to a chain length distribution of the fatty acid radical of the resulting amide amine from C8 to C18 with a maximum at C12.

The following epoxy-functional siloxanes were used in the preparation of the silicone quats:

TABLE 3

Epoxy-functional siloxanes of formula (VI)

| No. | a1 | a5 | b1 | b5 | c1 | c4 | d | $R^1$ | $R^{12}$ |
|---|---|---|---|---|---|---|---|---|---|
| SE1 | 0 | 2 | 48 | 0 | 0 | 0 | 0 | methyl | $-(CH_2)_3-O-CH_2-\underset{H}{\overset{O}{C}}-CH_2$ (glycidyl ether) |
| SE2 | 0 | 2 | 0 | 0 | 0 | 0 | 0 | methyl | $-(CH_2)_3-O-CH_2-\underset{H}{\overset{O}{C}}-CH_2$ |
| SE3 | 0 | 6 | 316 | 0 | 4 | 0 | 0 | methyl | $-(CH_2)_3-O-CH_2-\underset{H}{\overset{O}{C}}-CH_2$ |
| SE4 | 0 | 2 | 18 | 0 | 0 | 0 | 0 | methyl | $-(CH_2)_3-O-CH_2-\underset{H}{\overset{O}{C}}-CH_2$ |
| SE5 | 0 | 2 | 28 | 0 | 0 | 0 | 0 | methyl | $-(CH_2)_3-O-CH_2-\underset{H}{\overset{O}{C}}-CH_2$ |

Starting weights and further details of the preparation of the inventive siloxanes of formula (I) can be found in Tables 4 and 5.

TABLE 4

Part 1: Starting weights and further details of the preparation of the inventive siloxanes of formula (I) (content figures in % by weight based on the overall composition)

|  | I1 | I2 | I3 | I4 | I5 | I6 | I7 |
|---|---|---|---|---|---|---|---|
| SE1 | 860.2 g | | | | | | |
| SE2 | | 472.1 g | 393.4 g | 262.3 g | 262.3 g | 217.0 g | |
| SE3 | | | | | | | 297.7 g |
| SE4 | | | | | | | |
| Amide1 | 109.1 g | 39.3 g | | 21.8 g | 21.8 g | | 17.5 g |
| Amide2 | | | 39.6 g | | | 21.0 g | |
| Amide3 | | | | | | | |
| MDEA | 17.9 g | 6.4 g | 5.36 g | 3.6 g | 3.6 g | 2.9 g | 2.9 g |
| MDIPA | | | | | | | |
| DMAE | | | | | | | |
| HOAc | 30.9 g | 11.1 g | 9.3 g | 6.2 g | | 4.9 g | 4.9 g |
| INA | | | | | 16.3 g | | |
| IPA | 254.5 g | 132.2 g | 110.2 g | | 76 g | | 57.0 g |
| DPG | | | | 73.5 g | | | |
| tBuOH | | | | | | | |
| DMM | | | | | | 13.0 g | |
| Distillation | yes | yes | yes | no | yes | no | yes |
| Blend | yes | yes | yes | no | yes | yes | no |

TABLE 4-continued

Part 1: Starting weights and further details of the preparation of the inventive siloxanes of formula (I) (content figures in % by weight based on the overall composition)

|  | I1 | I2 | I3 | I4 | I5 | I6 | I7 |
|---|---|---|---|---|---|---|---|
| Active content[1] | 95% | 80% | 97.5% | 80% | 97.5% | 80% | 100% |
| Solvent | 5% PG | 20% DPG | 2.5% PG | 20% DPG | 2.5% PG | 15% DPG 5% DMM | |
| Epoxy conversion | 99% | 97% | 99% | 97% | 98% | 87% | 96% |
| Viscosity, 25° C., mPa*s | 3960 | 1605 | 7414 | 1102 | 4731 | 851 | n.d |
| Residual amide amine content | 0.4% | 0.17% | 0.35% | 0.6% | 0.4% |  | 0.3% |

TABLE 4

Part 2: Starting weights and further details of the preparation of the inventive siloxanes of formula (I) (content figures in % by weight based on the overall composition)

|  | I8 | I9 | I10 | I11 | I12 | I13 | I14 |
|---|---|---|---|---|---|---|---|
| SE1 |  |  |  |  |  |  |  |
| SE2 | 189.8 g | 419.7 g | 419.7 g | 288.5 g | 472.1 g | 239.9 g |  |
| SE3 |  |  |  |  |  |  |  |
| SE4 |  |  |  |  |  |  | 472.9 g |
| Amide1 | 15.3 g | 39.9 g | 39.9 g | 24.0 g |  |  |  |
| Amide2 |  |  |  |  |  | 23.7 g | 157.8 g |
| Amide3 |  |  |  |  | 41.1 g |  |  |
| MDEA | 2.5 g | 3.8 g | 3.8 g |  | 6.4 g |  | 21.9 g |
| MDIPA |  |  |  |  |  | 4.0 g |  |
| DMAE |  |  |  | 3.4 g |  |  |  |
| HOAc | 4.3 g | 9.9 g | 9.9 g | 4.8 g | 11.1 g | 5.6 g | 37.4 g |
| INA |  |  |  |  |  |  |  |
| IPA | 53 g | 118 g |  |  | 132.7 g | 68.3 g | 121.8 g |
| DPG |  |  |  |  |  | 67.9 g |  |
| tBuOH |  |  | 118 g | 80.2 g |  |  |  |
| DMM |  |  |  |  |  |  |  |
| Distillation | yes | yes | yes | yes | yes | yes | yes |
| Blend | yes | yes | yes | yes | yes | yes | yes |
| Active content[1] | 97.5% | 97.5% | 97.5% | 97.5% | 97.5% | 80% | 50% |
| Solvent | 2.5% PG | 2.5% PG | 2.5% PG | 2.5% PG | 2.5% PG | 20% DPG | 50% PG |
| Epoxy conversion | 99% | 98% | 96% | 98% | 99% | 96% | 100% |
| Viscosity, 25° C., mPa*s | 8746 | 9104 | 8546 | about 20000 | 7544 | 1217 |  |
| Residual amide amine content | 0.2% | 0.6% | 0.7% | 0.8% | 0.3% | 0.1% | 0.8% |

TABLE 4

Part 3: Starting weights and further details of the preparation of the inventive siloxanes of formula (I) (content figures in % by weight based on the overall composition)

|  | I15 | I16 |
|---|---|---|
| SE5 | 217.7 g | 217.7 g |
| Amide1 | 43.6 g |  |
| Amide2 |  | 52.6 g |
| MDEA | 7.2 g | 7.2 g |
| HOAc | 12.4 g | 12.4 g |
| IPA | 70.2 g | 72.5 g |
| Distillation | yes | yes |
| Blend | yes | yes |
| Active content[1] | 50% | 50% |
| Solvent | 50% PG | 50% PG |
| Epoxy conversion | 100% | 98% |
| Viscosity, 25° C., mPa*s | 705 | 616 |
| Residual amide amine content | 0.6% | 0.6% |

TABLE 5

Starting weights and further details of the preparation of non-inventive siloxanes (content figures in % by weight based on the overall composition)

|  | V1 | V2 | V3 | V4 |
|---|---|---|---|---|
| SE1 |  |  | 860.2 g |  |
| SE2 | 271.2 g | 314.6 g |  | 472.1 g |
| SE3 |  |  |  |  |
| Amide1 |  |  | 156 g | 56.1 g |
| Amide2 |  |  |  |  |
| MDEA |  | 14.3 g |  |  |
| TEA | 14.9 g |  |  |  |
| HOAc | 6.2 g | 7.4 g | 30.9 g | 11.1 g |
| INA |  |  |  |  |
| IPA | 73.0 g |  | 254.5 g | 132.2 g |
| tBuOH |  | 84.1 g |  |  |
| Distillation | yes | yes | yes | yes |
| Blend | no | yes | yes | yes |
| Active content[1)] |  | 97.5% | 95% | 97.5% |
| Solvent |  | 2.5% PG | 5% PG | 2.5% PG |
| Epoxy conversion | 0% biphasic | 92.3% | 98% | 97% |
| Viscosity, 25° C., mPa*s | — | 8429 | 4631 | 9114 |
| Residual amide amine content | — | — | 1.8% | 1.4% |

[1)]active content = proportion by mass of the siloxanes (active ingredients) based on the total mass of the composition In the synthesis of inventive examples I1 to I14, mixtures of dialkanolamines and amide amines were used. In the case of comparative examples V1 and V2 by contrast, no amide amines but only alkanolamines were used, specifically a trialkanolamine in V1 and a dialkanolamine in V2. In the synthesis of comparative examples V3 and V4, again, exclusively amide amines and no alkanolamines were used. The non-inventive siloxane compositions V3 and V4 had a higher residual content of amide amine than the inventive siloxane compositions I1 to I14. In the case of V1 a phase separation was observed: no reaction of the epoxy-functional siloxane with the alkanolamine was detectable. In the case of V2, by contrast, epoxy conversion was observed, and so a reaction took place here. Since amide amines were not used either in V1 or V2, there is no need to state a residual content.

A non-inventive blend of 70 parts V4 with 30 parts V2 was prepared by stirring with a magnetic stirrer bar at room temperature in a sample bottle and subjected to HPLC analysis. The measurement of the residual amide amine content gave 0.8%, compared to the theoretical 0.9%. The inventive product 15 that was prepared by reaction of the same SE2 precursor with a mixture of 0.7 molar equivalent of Amide1 and 0.3 molar equivalent of MDEA based on 1 molar equivalent of epoxy groups has a residual amide amine content measured by HPLC of 0.4%. The solvent content of the mixture of V4 and V2 and in the case of 15 corresponded to 2.5% PG in al cases. This comparison shows that the inventive preparation of the novel mixed-functionality silicone quats and the compositions thereof achieves significantly lower residual amide amine contents than are achievable in comparison via the obvious blending.

Storage Stability Tests on the Silicone Quats:

Two 100 ml screwtop sample bottles in each case were each half-filled with the silicone quats I5. I6 and I7. One sample bottle was stored closed at room temperature (RT) and the respective second sample bottle was stored closed in a conventional laboratory drying cabinet from Binder at 50° C. After defined storage periods, the viscosity of the samples was determined at 25° C. and/or the content of cyclic siloxanes was checked by GC analysis. For better comparability and measurability, the 100% silicone quat 17, which had a high viscosity, was blended with 20% DPG to active content 80%. The results of the storage stability tests are summarized in Table 6.

TABLE 6

Results of the storage stability tests on the silicone quats (content figures in % by weight based on the overall composition)

| Sample | Storage period | Storage temperature | Viscosity at 25° C. [mPa*s] | D4 content [% by wt.] |
|---|---|---|---|---|
| I5 | 0 week | RT | 4731 | 0.02 |
| I5 | 4 weeks | RT | n.d | 0.02 |
| I5 | 12 weeks | RT | n.d | 0.03 |
| I5 | 4 weeks | 50° C. | n.d | 0.06 |
| I6 | 0 week | RT | 851 | 0.08 |
| I6 | 4 weeks | RT | 1031 | 0.08 |
| I6 | 12 weeks | RT | 1093 | 0.08 |
| I7-80% | 0 week | RT | 6396 | 0.09 |
| I7-80% | 4 weeks | RT | 5330 | 0.09 |
| I7-80% | 8 weeks | RT | 6001 | 0.09 |
| I7-80% | 12 weeks | RT | 6888 | 0.09 |

The storage tests show that there are no significant changes in viscosity and the silicone quats can still be metered efficiently even after prolonged storage time. In addition, the storage tests show that the new formation of cyclic siloxanes during the storage time is minimized, in that an increase in D4 of ≤0.05% by weight is detected. Sample 5, which was distilled particularly thoroughly, shows that the proportion of D4 is <0.1% by weight over a prolonged storage period. The content of D4 in the respective sample depends on the quality of distillation in the preparation and not on the storage time.

Application Examples

Materials Used:

TABLE 7

Emulsifiers

| Emulsifiers | Trade name |
|---|---|
| C12-15 Pareth-7 / 9 / 12 | Tomadol ® 25-7, Evonik |
|  | Tomadol ® 25-9, Evonik |
|  | Tomadol ® 25-12, Evonik |
| Isotridecanol-6 / 8 / 12 | Lutensol ® TO 6, BASF |
|  | Lutensol ® TO 8, BASF |
|  | Marlipal ® O13/120, BASF |
| Laureth-6 / 12 | Lutensol ® AO 6, BASF |
|  | Marlipal 24/120, Sasol |
| Sorbitan sesquioctanoate | TEGO ® SQS 25, Evonik |
| Methyldiisopropanolamine ester quat | REWOQUAT ® CR 3099, Evonik |

TABLE 8

Auxiliaries

| Further silicone compounds | Trade name |
|---|---|
| Alkyl/polyether-modified silicone copolymer | TEGOPREN ® 7008, Evonik |
|  | TEGOPREN ® 7009, Evonik |

Fabric:

Textiles: cotton fabric (basis weight 205 g/m$^2$, thickness: 400 μm); polyester blend fabric (65% by weight of polyester and 35% by weight of cotton, basis weight 170 g/m$^2$, thickness: 200 μm); polyamide fabric (nylon-6,6, basis weight 65 g/m², thickness: 50 μm); all samples from WFK-Testgewebe GmbH (Christenfeld 10 41379 Brüggen).

Formulation and Finishing:

Production of the Emulsions:

The synthesized siloxane compositions selected from I1 to I14 (based on mixtures of alkanolamine and amide amine), V2 (based on alkanolamine), V4 (based on amide amine) and V5 (Magnasoft® DerMa NT as commercial comparative product) were initially charged and, if required, diluted further by addition of a glycol to the desired active content, i.e. the desired proportion by mass of active ingredient (siloxane). This was found to be advantageous since particularly good results were achieved when the active ingredients were converted further from a solvent, especially when they are used as mixtures with solvents having an active content of 80%. Thereafter, the mixtures RE1 to RE10 thus obtained were initially charged and the emulsifiers and any further auxiliaries and/or glycols were added. Then water was added gradually while stirring constantly with a propeller stirrer. The pH was adjusted to a pH of about 4 by subsequent addition of acetic acid. Stirring was continued until the mixture is homogeneous. In this way, the emulsions 11 to 126 and C1 to C5 were obtained.

Padding Method (Model: HVF, Mathis AG):

To test the respective emulsions, a liquor that contained 8 g/l of the appropriate emulsion in each case was applied to the above-described fabric, which was squeezed off to a wet pickup of about 70% to 80% by weight and dried. The values employed for pressure and speed can be found in Table 9. Padding application took place at room temperature.

TABLE 9

Pressures and roll speeds used in the padding method.

| Designation | Pressure [bar] | Speed [m/min] |
| --- | --- | --- |
| Cotton fabric | 2.4-5.8 | 2 |
| Polyester blend fabric | 1.0-1.2 | 2 |
| Polyamide fabric | 1.0 | 1-2 |

Exhaust Process Starting from Solvent-Containing Formulations:

To test the active ingredients, the abovementioned fabrics were finished with a liquor that contained 20 g/l of the appropriate active ingredient in each case. A liquor ratio (fabric to liquor) of 1:15 was chosen. Solvents used are water, butyl acetate and ethyl acetate. The test fabric was treated in the liquor with continuous agitation on the reciprocating shaker (model: 3006, manufacturer GFL) for 30 min. After 30 min, the test fabric was removed from the bath, wrung out gently, shaken and dried. A blank was treated under the same conditions with demineralized water only.

Drying Method (LTE Lab Dryer, Mathis AG, Ventilator Speed 2000 Rpm):

The fabrics were dried at 105° C. (plus dwell time, i.e. the heating time of the textile fabric) for 2 min and then condensed at 160° C. to 180° C. (without dwell time) for 0.5 min to 1 min in order to fix the finish. The exact conditions are summarized in Table 10.

TABLE 10

Conditions for the drying process

|  | Drying | | Fixing | |
| --- | --- | --- | --- | --- |
|  | [° C.] | [min] | [° C.] | [min] |
| Cotton fabric (exhaust) | 105 | 2.0 | 160 | 1.0 |
| Polyester blend fabric (exhaust) | 105 | 2.0 | 180 | 0.5 |
| Polyamide fabric (exhaust) | 105 | 2.0 | 180 | 0.5 |
| Cotton fabric (padding) | 105 | 2.0 | 150 | 3.0 |
| Polyester blend fabric (padding) | 105 | 2.0 | 150 | 3.0 |
| Polyamide fabric (padding) | 105 | 2.0 | 150 | 3.0 |

Testing of the Finish:

Hand:

Hand is a fundamental quality parameter of a fabric. It can be described by, for example, smoothness, compressibility and stiffness. Normally, hand is determined by subjective assessment via manual testing. In addition, there are measuring instruments for the purpose that determine it objectively.

Assessment of Hand (Hand Test) Via Measuring Instruments (TSA Value/Handfeel):

A piece of textile fabric that has been cut to size, after prior conditioning (4 hours) at 25° C. and 50% relative air humidity, was inserted and clamped into the TSA (Tissue Soft Analyzer, from Emtec Electronic GmbH). The test instrument then determines individual values for softness, smoothness and stiffness of the textile fabric and uses these to ascertain the overall impression, the handfeel (HF). This TSA value (HF value) was ascertained by means of an algorithm specially designed for textiles by EMTEC. A higher HF value means a higher softness. The assessments are made in comparison to an analogous treatment without active ingredient.

Assessment of Hand (Hand Test) by Hand (Panel Test):

To assess hand, an experienced team of 10 specialists was assembled, who assessed the anonymized hand specimens, the abovementioned fabrics that had been finished with the emulsions, with the aid of a hand panel test on a scale of 1 to 5, with the mark 1 meaning very poor hand and the mark 5 very good hand. The result of the panel test is reported as the average of all assessments. For the hand specimens made of knitted fabric, an inconspicuously labelled untreated sample was additionally included.

Antistatic Properties:

Antistatic properties are measured in accordance with DIN 54345 T.1 (ring electrode) with measurement voltage 100 V (Tera-Ohm-Meter 6206 instrument). The finish with antistats reduces the electrical resistance on textile fabrics. The reduction in the resistance is a measure of antistatic efficacy.

The antistatic properties were determined using the following instruments and fabrics:

Standard test fabric: polyester (100%, 30 A type from wfk/Krefeld)
Washing machine for pretreatment and padding for finishing of the fabric
Climate-controlled room (23±1° C., 50-60% r.h.)
Tera-Ohm-Meter 6206 (from Eltex)
6216 test electrode (from Eltex) to DIN 54345 T.1

Prior to the measurement, the finished fabrics are stored in the climate-controlled room for one day in order to assure balanced moisture. 10×15 cm pieces are placed onto a flat surface and the ring electrode is positioned thereon. The resistance of the different finishes is measured.

Application Results:

The synthesis products I3 to I12 and V2 and V4, and also a comparative product V5 which is customary on the market, if the active content was not already 80% by weight based on the composition, were brought to a homogeneous active content of 80% by addition of butyldiglycol (BDG). The mixtures RE1 to RE10 thus obtained are summarized in Table 8. These mixtures were used as described above to produce the emulsions I1 to I26 and C1 to C12. The compositions of the emulsions and the properties thereof are summarized in the tables which follow.

TABLE 11

Preliminary mixtures for the comparative performance testing

| | RE8 | RE1 | RE2 | RE4 | RE5 | RE6 | RE7 | RE3 | RE9 | RE10 |
|---|---|---|---|---|---|---|---|---|---|---|
| Siloxane | I3 | I4 | I8 | I9 | I10 | I11 | I12 | V2 | V4 | V5 |
| Additional solvent | BDG | — | BDG | BDG | BDG | BDG | BDG | BDG | BDG | BDG |

TABLE 12

Inventive emulsions and their properties (content figures in % by weight based on the overall composition)

| % | I1 | I2 | I3 | I4 | I5 |
|---|---|---|---|---|---|
| RE8 | 18.2 | 23.8 | 32.5 | 25 | 25 |
| TEGOPREN ® 7008 | 5.6 | — | — | — | — |
| TOMADOL ® 25-7 | 7.7 | — | — | — | 1.7 |
| TOMADOL ® 25-9 | — | 2.5 | — | 1.5 | — |
| TOMADOL ® 25-12 | — | — | — | — | 3.4 |
| TEGO ® SQS 25 | — | 2.5 | 5.5 | — | — |
| REWOQUAT ® CR 3099 | — | — | 5.7 | — | — |
| Butyldiglycol | 8.6 | — | — | 10.0 | — |
| Dipropylene glycol | — | 5.0 | 15.0 | — | — |
| Water | 60.1 | 66.2 | 41.4 | 63.2 | 69.6 |
| Acetic acid | 0.3 | — | — | 0.3 | 0.3 |
| Appearance | clear solution | milky white | clear solution | clear solution | opaque |
| Emulsion type | micro-emulsion | macro-emulsion | micro-emulsion | micro-emulsion | micro-emulsion |
| Property | bulky | bulky | substantive | cost-efficient | solvent-reduced |
| Hand test (TSA value) | 39.2 | 38.8 | 38.4 | 37.6 | 37.2 |

TABLE 13

Non-inventive emulsions and their properties (content figures in % by weight based on the overall composition)

| % | C1 | C2 | C3 | C4 | C5 |
|---|---|---|---|---|---|
| RE9 | 18.2 | 23.8 | 32.5 | 25 | 25 |
| TEGOPREN ® 7008 | 5.6 | — | — | — | — |
| TOMADOL ® 25-7 | 7.7 | — | — | — | 1.7 |
| TOMADOL ® 25-9 | — | 2.5 | — | 1.5 | — |
| TOMADOL ® 25-12 | — | — | — | — | 3.4 |
| TEGO ® SQS 25 | — | 2.5 | 5.5 | — | — |
| REWOQUAT ® CR 3099 | — | — | 5.7 | — | — |
| Butyldiglycol | 8.6 | — | — | 10.0 | — |
| Dipropylene glycol | — | 5.0 | 15.0 | — | — |
| Water | 60.1 | 66.2 | 41.4 | 63.2 | 69.6 |
| Acetic acid | 0.3 | — | — | 0.3 | 0.3 |
| Appearance | clear solution | milky white | clear solution | clear solution | opaque |
| Emulsion type | micro-emulsion | macro-emulsion | micro-emulsion | micro-emulsion | micro-emulsion |
| Property | bulky | bulky | substantive | cost-efficient | solvent-reduced |
| Hand test (TSA value) | 37.4 | 37.0 | 37.3 | 36.5 | 36.3 |

The inventive emulsions I1 to I5 from Table 12 differ from the corresponding non-inventive emulsions C1 to C5 from Table 13 only in the active ingredient used, with otherwise identical composition. The inventive emulsions by comparison with the non-inventive emulsions show distinctly improved TSA values (HF values, handfeel). The improved hand properties were confirmed in panel tests. As well as handfeel, good water absorption is also of relevance for wear comfort. Finishing with the inventive emulsions does not show any disadvantages here compared to finishing with emulsions based on prior art active ingredients. According to the material quality (thickness and weave type) and formulation, it is even possible to achieve better water absorption capacities or water retention capacities. Water absorption capacity or water retention capacity is additionally also affected by the choice of emulsifiers used.

TABLE 14

Inventive emulsions comprising auxiliaries for improvement of bulkiness and properties thereof (content figures in % by weight based on the overall composition)

| % | I6 | I7 | I8 | I9 | I10 | I11 |
|---|---|---|---|---|---|---|
| RE0 | 20 | — | 20 | — | 20 | — |
| RE1 | — | 20 | — | 20 | — | 20 |
| TEGOPREN ® 7008 | 4.0 | 4.0 | — | — | — | — |
| TEGOPREN ® 7009 | — | — | 4.0 | 4.0 | — | — |
| Lutensol ® TO 8 | 1.5 | 1.5 | 1.5 | 1.5 | 1.5 | 1.5 |
| Butyldiglycol | 10.0 | 10.0 | 10.0 | 10.0 | 10.0 | 10.0 |
| Dipropylene glycol | 5.5 | 5.5 | 5.5 | 5.5 | 5.5 | 5.5 |
| Water | 58.7 | 58.7 | 58.7 | 58.7 | 58.7 | 58.7 |
| Acetic acid | 0.3 | 0.3 | 0.3 | 0.3 | 0.3 | 0.3 |
| Appearance | clear solution | clear solution | separation | separation | clear solution | clear solution |
| Hand test (TSA value) | 39.3 | 38.1 | 38.0 | 38.4 | 36.8 | 37.2 |
| Panel test (1-5; 5 = best mark) | 5 | 4.3 | 4.3 | 4.3 | 3.8 | 4.0 |

Table 14 shows that the additional use of auxiliaries/additives for improving bulkiness (Tegopren® 7008 and Tegopren® 7009) can further improve the assessments of hand. This is equally true of assessments of hand that have been determined by means of measuring instruments (TSA value, handfeel) and by hand (panel test). The active ingredients according to the invention, in combination with an auxiliary/additive for improving bulkiness, show the best results when they have been converted from a solvent, especially when they have been used as mixtures with an active content of 80%. This finish is also impressive in an assessment of hand in a panel test.

TABLE 15

Emulsions with cost-optimized auxiliaries and their properties (content figures in % by weight based on the overall composition)

| % | I12 | C6 | I13 | I14 | C7 | I15 |
|---|---|---|---|---|---|---|
| RE2 | 20.5 | — | — | — | — | — |
| RE3 | — | 20.5 | — | — | — | — |
| RE4 | — | — | 20.5 | — | — | — |
| RE5 | — | — | — | 20.5 | — | — |
| RE9 | — | — | — | — | 20.5 | — |
| RE6 | — | — | — | — | — | 20.5 |
| Isotridecanol 8EO | 1.5 | 1.5 | 1.5 | 1.5 | 1.5 | 1.5 |
| Butyldiglycol | 10.0 | 10.0 | 10.0 | 10.0 | 10.0 | 10.0 |
| Dipropylene glycol | 4.5 | 4.5 | 4.5 | 4.5 | 4.5 | 4.5 |
| Water | 63.2 | 63.2 | 63.2 | 63.2 | 63.2 | 63.2 |
| Acetic acid | 0.3 | 0.3 | 0.3 | 0.3 | 0.3 | 0.3 |
| Appearance | clear solution | separation | clear solution | clear solution | separation | clear solution |
| Hand test (TSA value) | 38.5 | 37.3 | 37.1 | 36.7 | 37.3 | 37.6 |

Table 15 shows that, when cost-optimized auxiliaries are used, such as isotridecanol 8EO, very good assessments of hand are likewise achieved in the case of the emulsions according to the invention, without observation of phase separation.

TABLE 16

Inventive and non-inventive emulsions comprising additives for improvement of bulkiness and properties thereof (content figures in % by weight based on the overall composition)

| % | I16 | C8 | I17 | I18 | C10 | I19 |
|---|---|---|---|---|---|---|
| RE2 | 18.5 | — | — | — | — | — |
| RE3 | — | 18.5 | — | — | — | — |
| RE4 | — | — | 18.5 | — | — | — |
| RE5 | — | — | — | 18.5 | — | — |
| RE9 | — | — | — | — | 18.5 | — |
| RE6 | — | — | — | — | — | 18.5 |
| TEGOPREN ® 7008 | 5.6 | 5.6 | 5.6 | 5.6 | 5.6 | 5.6 |
| Rewopal ® LA6 | 7.7 | 7.7 | 7.7 | 7.7 | 7.7 | 7.7 |
| Butyldiglycol | 5.0 | 5.0 | 5.0 | 5.0 | 5.0 | 5.0 |
| Water | 62.9 | 62.9 | 62.9 | 62.9 | 62.9 | 62.9 |
| Acetic acid | 0.3 | 0.3 | 0.3 | 0.3 | 0.3 | 0.3 |
| Appearance | clear solution | separation | clear solution | clear solution | clear solution | clear solution |
| Hand test (TSA value) | 38.3 | 37.9 | 37.3 | 38.2 | 37.4 | 37.3 |

Table 16 shows the advantages of the emulsions according to the invention. The non-Inventive emulsion C8 shows good results in the hand test and no residual content of amide amines since it is based on an active ingredient (V2) that has been prepared solely from alkanolamines as tertiary amines. But emulsion C8 has the disadvantage that a phase separation is observed. Conversely, there is no phase separation in the case of non-inventive emulsion C10; instead, a clear solution is obtained. However, the assessment of hand here is much poorer. Since the emulsion is additionally based on an active ingredient (V4) that has been prepared solely from amide amines as tertiary amines, the residual content of amide amines is high. The compositions according to the invention lead to advantageous phase characteristics, a low residual content of amide amines, and a very good assessment of hand.

I12 and I16 show a particularity good assessment of hand as well as good formability.

TABLE 17

Inventive emulsions and their properties - effect on chain length of the fatty acid or of the alkoxylate (content figures in % by weight based on the overall composition)

| % | I20 | I21 | I22 |
|---|---|---|---|
| RE2 | 20.5 | — | — |
| RE7 | — | 20.5 | — |
| RE8 | — | — | 20.5 |
| Lutensole ® TO 8 | 1.5 | 1.5 | 1.5 |
| Dipropylene glycol | 4.5 | 4.5 | 4.5 |
| Butyldiglycol | 10.0 | 10.0 | 10.0 |
| Water | 63.2 | 63.2 | 63.2 |
| Acetic acid | 0.3 | 0.3 | 0.3 |
| Appearance | clear solution | clear solution | clear solution |
| Hand test (TSA value) | 37.2 | 37.5 | 37.6 |

Table 17 shows the effect of different fatty acid amides (I20: cocoyl, I21: palmityl, I22: stearyl). Irrespective of the choice of fatty acid amide, very good results are obtained in the hand test. In addition, it is found that the longer the alkyl chain length of the acid radical of the amide amine, the better the assessments in the hand test. This correlation was also confirmed in the panel test.

TABLE 18

Emulsions and their properties (content figures in % by weight based on the overall composition)

| % | I23 | C11 | C12 |
|---|---|---|---|
| RE8 | 20.5 | — | — |
| RE9 | — | 20.5 | — |
| RE10 | — | — | 20.5 |
| Isotridecanol 6EO | 10.5 | 10.5 | 10.5 |
| Isotridecanol 12EO | 1.8 | 1.8 | 1.8 |
| Water | 66.8 | 66.8 | 66.8 |
| Acetic acid | 0.4 | 0.4 | 0.4 |
| Appearance | clear solution | clear solution | clear solution |
| Hand test (TSA value) | 37.9 | 37.5 | 36.7 |
| Panel test (1-5; 5 = best) | 4.8 | 4.5 | 4.0 |

The results in Table 18 show that the use of the active ingredients according to the invention leads to a better assessment of hand compared to non-inventive active ingredients, especially to commercially available active ingredients.

TABLE 19

Inventive emulsions comprising additives for improvement of bulkiness and properties thereof (content figures in % by weight based on the overall composition)

| % | I24 | I25 | I26 |
|---|---|---|---|
| RE2 | 20.5 | — | — |
| RE7 | — | 20.5 | — |
| RE8 | — | — | 20.5 |
| TEGOPREN ® 7008 | 5.6 | 5.6 | 5.6 |
| Dodecanol 6EO | 7.7 | 7.7 | 7.7 |
| Dipropylene glycol | 3.3 | 3.3 | 3.3 |
| Butyldiglycol | 5.0 | 5.0 | 5.0 |
| Water | 63.5 | 63.5 | 63.5 |
| Appearance | clear solution | clear solution | clear solution |
| Hand test (TSA value) | 36.8 | 37.3 | 37.6 |

The results in Table 19 also make it clear that the use of siloxanes according to the invention leads to a better assessment of hand.

It should be emphasized that the use of the siloxanes according to the invention leads to a better assessment of hand, better phase characteristics and/or a lower amide amine content.

To test the antistatic properties, the silicone quats were diluted in demineralized water to an active content of 20% by weight and then applied to the polyester fabric by a padding operation by the method described above.

TABLE 20

Antistatic compositions (content figures in % by weight based on the overall composition)

|  | C13 | I27 | C14 | C15 | I28 |
|---|---|---|---|---|---|
| Silicone quat | 40% V6 [2)] | 40% I14 [3)] | 21% V7 [4)] | 25% V8 [5)] | 25% REB [6)] |
| Water | 60% | 60% | 79% | 75% | 75% |
| Active content | 20% | 20% | 20% | 20% | 20% |
| Appearance | clear | opaque | milky | milky | biphasic |

[2)] Composition comprising a silicone quat prepared from Amide1 and SE4 (b1 = 18)
[3)] Composition comprising a silicone quat prepared from Amide2 and SE4 (b1 = 18)
[4)] Composition comprising a silicone quat prepared from Amide1 and SE2 (b1 = 78)
[5)] Composition comprising a silicone quat prepared from Amide1 and SE2 (b1 = 78)
[6)] Composition comprising a silicone quat prepared from Amide2 and SE2 (b1 = 78)

Comparison of I27 with C13 and of I28 with C14 and C15 shows that, given the same siloxane chain length, somewhat poorer solubility is observed in the case of the inventive compositions I27 and I28. When used as active antistatic and glidant ingredient, however, the somewhat poorer solubility reduces unwanted penetration of the product into the textile fibre matrix. The active antistatic ingredient remains on the surface to a greater degree than in the comparative examples and leads to a better gliding effect coupled with a similar antistatic effect. In order to compare the products, no further auxiliaries that are typically used in spinning preparations were used. In the case of I28, a phase separation was observed. For this reason, no antistatic measurements were conducted therefor.

TABLE 21

Antistatic properties

|  | Resistance in Ω (0.01 g of sample/ 1 g of textile) | Resistance in Ω (0.02 g of sample/ 1 g of textile) | Resistance in Ω (0.03 g of sample/ 1 g of textile) |
|---|---|---|---|
| C13 | 5.94E+08 | 4.75E+08 | 2.80E+07 |
| I27 | 2.29E+09 | 1.37E+09 | 4.96E+08 |
| C14 | 1.03E+10 | 2.81E+10 | 2.02E+10 |
| C15 | 9.05E+10 | 3.83E+10 | 8.41E+09 |
| I28 | not determined | not determined | not determined |
| Blank [7)] | 4.13E+11 | 4.13E+11 | 4.13E+11 |

[7)] Value for the untreated polyester fabric

The samples comprising short-chain siloxanes C13 and I27 show an adequate antistatic effect. The antistatic properties of inventive example I27 are somewhat less than in the case of non-inventive example C13. This difference is acceptable and is more than compensated for by the better gliding effect and better hand of the inventive example. The inventive example has less of a tendency to penetrate into the fabric and hence improves the hand. Resistance is determined under the idealized boundary conditions that are to be observed according to the DIN cited. In industrial application, however, it is found that the antistatic finish in the case of C13 declines with time, whereas the antistatic properties of I27 remain largely unchanged. It is assumed that the elevated friction under real conditions leads to elevated penetration of the non-inventive sample into the textile, such that the antistatic finish declines with time. The product according to the invention, by contrast, has less of a tendency to penetrate and leads to a substantially constant finish under stress conditions that are customary in production.

Water-Thinnable Formulations for Automotive Care:
Materials Used:
  Carspray 90 Di-(Oleyl carboxyethyl) Hydroxyethyl Methylammonium Methosulfate
  REWOCARE DOC diethylhexyl carbonate
  TEGO POLISH ADDITIV 5 decamethylcyclopentasiloxane, D5
  REWOPAL MPG 40 tetraethylene monophenyl ether
  DPG dipropylene glycol
  TEGOPREN 6922 Quaternium 80 (silicone quat)
  REWOQUAT CR 3099 Di Oleic Acid Isopropylester Dimethylammonium Methosulfate
  Butyl Cellosolve 2-butylethanol
  REWOCARE OT isooctyl Tallowate

TABLE 22

Automotive care formulations (content figures in parts by weight)

| Constituent | Formulation with benchmark | Formulation with I15 | Formulation with I16 |
|---|---|---|---|
| Carspray 90 | 12 parts | 12 parts | 12 parts |
| REWOCARE ® DOC | 5 parts | 5 parts | 5 parts |
| D5 | 2 parts | 2 parts | 2 parts |
| REWOPAL ® MPG 40 | 6 parts | 6 parts | 6 parts |
| DPG | 8 parts | 8 parts | 8 parts |
| TEGOPREN ® 6922 | 0.8 part | | |
| I15 | | 0.8 part | |
| I16 | | | 0.8 part |
| Water | 65.7 parts | 65.7 parts | 65.7 parts |
| Acetic acid, conc. | 0.5 part | 0.5 part | 0.5 part |

TABLE 23

Automotive care formulations (content figures in parts by weight)

| Constituent | Formulation with benchmark | Formulation with I15 | Formulation with I16 |
|---|---|---|---|
| REWOQUAT ® CR 3099 | 10 parts | 10 parts | 10 parts |
| REWOPAL ® MPG 40 | 8.6 parts | 8.6 parts | 8.6 parts |
| Butyl Cellosolve | 6.2 parts | 6.2 parts | 6.2 parts |
| REWOCARE ® OT | 8 parts | 8 parts | 8 parts |
| D5 | 3 parts | 3 parts | 3 parts |
| TEGOPREN ® 6922 | 0.8 part | | |
| I15 | | 0.8 part | |
| I16 | | | 0.8 part |
| Water | 62.9 parts | 62.9 parts | 62.9 parts |
| Acetic acid, conc. | 0.5 part | 0.5 part | 0.5 part |

These automotive care formulations were tested for water thinnability by diluting 1 part automotive care formulation (see Tables 22 and 23) with 26 parts water. There must be no apparent cloudiness.

TABLE 24

Basis formulations for fabric softeners (without perfume, colour and other additives) (content figures in parts by weight)

| Constituent | Formulation with benchmark | Formulation with I3 |
|---|---|---|
| SQ1 | 0.15 | |
| I3 | | 0.15 part |
| REWOQUAT ® WE 18 | 5.65 parts | 5.65 parts |
| Water | 94.2 parts | 94.2 parts |

The invention claimed is:

1. A siloxane (A) of formula (I):

$$M^1_{a1}M^2_{a2}M^3_{a3}M^4_{a4}D^1_{b1}D^2_{b2}D^3_{b3}T^1_{c1}T^4_{c4}Q_d \quad \text{Formula (I)},$$

with
- $M^1=[R^1_3SiO_{1/2}]$;
- $M^2=[R^2R^1_2SiO_{1/2}]$;
- $M^3=[R^3R^1_2SiO_{1/2}]$;
- $M^4=[R^4R^1_2SiO_{1/2}]$;
- $D^1=[R^1_2SiO_{2/2}]$;
- $D^2=[R^1R^2SiO_{2/2}]$;
- $D^3=[R^1R^3SiO_{2/2}]$;
- $T^1=[R^1SiO_{3/2}]$;
- $T^4=[R^4SiO_{3/2}]$;
- $Q=[SiO_{4/2}]$;
- $a1=0$ to 32;
- $a2=0$ to 32;
- $a3=0$ to 32;
- $a4=0$ to 6;
- $b1=1$ to 1000;
- $b2=0$ to 10;
- $b3=0$ to 10;
- $c1=0$ to 10;
- $c4=0$ to 5;
- $d=0$ to 10;
- $R^1$=each independently identical or different hydrocarbon radicals;
- $R^2=R^{21}$-$R^{22}$;
- $R^{21}$ each independently identical or different divalent hydrocarbon radicals having at least one hydroxyl group and optionally further oxygen atoms;
- $R^{22}$ each independently identical or different radicals of formula (II)

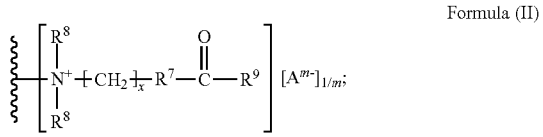

Formula (II)

- $R^3=R^{31}$-$R^{32}$;
- $R^{31}=R^{21}$;
- $R^{32}$=each independently identical or different radicals of formula (III)

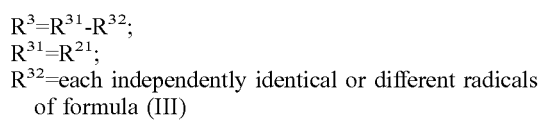

Formula (III)

- $R^4$=each independently identical or different alkoxy groups or acyloxy groups;
- $R^7$=—NH—;
- $R^8$=each independently identical or different radicals selected from the group consisting of methyl, ethyl n-propyl, isopropyl, n-butyl, isobutyl, and tert-butyl;
- $R^9$=each independently identical or different hydrogen and hydrocarbon radicals having 1 to 30 carbon atoms;
- $R^{11}$=each independently identical or different hydrocarbon radicals having at least one hydroxyl group and from 1 to 6 carbon atoms;
- $(A1)^{m-}$=each independently identical or different inorganic or organic anions with a charge of m−,
- m 1 to 3; and
- x=3;

wherein conditions (i) and (ii) are applicable:

$$a2+b2 \geq 1; \text{ and} \quad \text{(i)}$$

$$a3+b3 \geq 1. \quad \text{(ii)}$$

2. The siloxane (A) according to claim 1, wherein in addition, either condition (iii) or condition (iv) is applicable:

$$a1=a4=b2=b3=c1=c4=d=0, \text{ and} \quad \text{(iii)}$$

$$a2=a3=1; \text{ or}$$

$$b2=b3=0, \quad \text{(iv)}$$

$$c1+c4+d \geq 1, \text{ and}$$

$$a2+a3+a4 \geq 3.$$

3. A composition, comprising:
at least one siloxane (A) according to claim 1.

4. The composition according to claim 3, wherein the composition additionally comprises:
at least one siloxane selected from the group consisting of siloxane (B) and siloxane (C), wherein:
the siloxane (B) is a siloxane that differs from the siloxane (A) at least in that conditions (v) and (vi) are applicable rather than the conditions (i) to (ii):

$$a2=b2=0, \text{ and} \quad \text{(v)}$$

$$a3+b3 \geq 2; \text{ and} \quad \text{(vi)}$$

the siloxane (C) is a siloxane that differs from the siloxane (A) at least in that conditions (vii) and (viii) are applicable rather than conditions (i) and (ii):

$$a3=b3=0, \text{ and} \quad \text{(vii)}$$

$$a2+b2 \geq 2. \quad \text{(viii)}$$

5. The composition according to claim 4, wherein
a. a proportion by mass (% by weight) of the at least one siloxane (A) based on the total mass of the siloxanes is from 20% to 70%; and/or
b. a proportion by mass (% by weight) of the siloxane (B) based on the total mass of the siloxanes is from 0% to 15%; and/or
c. a proportion by mass (% by weight) of the siloxane (C) based on the total mass of the siloxanes is from 3% to 80%.

6. The composition according to claim 3, wherein the composition comprises amide amines, wherein a proportion by mass (% by weight) of the amide amines based on the total mass of the at least one siloxane (A) is less than 1%.

7. A process for preparation of the siloxane (A) according to claim 1 or of a composition comprising the siloxane (A), the process comprising:
reacting at least one epoxy-functional siloxane having at least two epoxy groups with at least one tertiary amine selected from the group consisting of amide amines, and
at least one tertiary amine selected from the group consisting of dialkanolamines,
to form quaternary ammonium groups.

8. The process according to claim 7, wherein the at least one epoxy-functional siloxane is prepared by hydrosilylation of at least one olefinically unsaturated epoxide with at least one SiH-functional siloxane of formula (V)

$$M^1{}_{a1}M^5{}_{a5}D^1{}_{b1}D^5{}_{b5}T^1{}_{c1}T^4{}_{c4}Q_d \quad \text{Formula (V)},$$

with
$M^5 = [R^1{}_2 SiHO_{1/2}]$,
$D^5 = [R^1 SiHO_{2/2}]$,
a5=0 to 32;
b5=0 to 10;
where
$M^1, D^1, T^1, T^4, Q$, a1, b1, c1, c4, d, and $R^1$ are as defined in formula (I).

9. The process according to claim 7, wherein the at least one epoxy-functional siloxane is a siloxane of the formula (VI)

$$M^1{}_{a1}M^6{}_{a5}D^1{}_{b1}D^6{}_{b5}T^1{}_{c1}T^4{}_{c4}Q_d \quad \text{Formula (VI)},$$

with
$M^6 = [R^{13}R^1{}_2 SiO_{1/2}]$,
$D^6 = [R^{13}R^1 SiO_{2/2}]$,
a5=0 to 32,
b5=0 to 10,
$R^{13}$=each independently identical or different organic epoxy radicals
wherein
$M^1, D^1, T^1, T^4, Q$, a1, b1, c1, c4, d, and $R^1$ are as defined in formula (I).

10. The process according to claim 7, wherein a residual content of the at least one tertiary amine selected from the group consisting of amide amines after the reaction, as a proportion by mass (% by weight) based on the total mass of the composition, is less than 1%.

11. The process according to claim 7, wherein the at least one tertiary amine selected from the group consisting of amide amines is a tertiary amine of formula (VII)

Formula (VII)

wherein $R^8, R^7, R^9$, and x are as defined in formula (II).

12. The process according to claim 7, wherein the at least one tertiary amine selected from the group consisting of dialkanolamines is a tertiary amine of formula (VIII)

Formula (VIII)

wherein $R^8$ and $R^{11}$ are as defined in formula (III).

13. A composition obtainable by the process according to claim 7.

14. A composition, comprising:
water, and
at least one siloxane (A) according to claim 1 or a composition comprising the at least one siloxane (A).

15. A method, comprising:
a) treating two-dimensional structures;
b) producing cleaning and care formulations for household and for industrial purposes;
c) producing cosmetic, pharmaceutical, and dermatological compositions; and/or
d) cleaning hard surfaces,
with the siloxane (A) according to claim 1.

16. The siloxane (A) according to claim 1, wherein
a1=0 to 12;
a2=1 to 3;
a3=1 to 2;
a4=0;
b1=10 to 400;
b2=0;
b3=0,
c1=0 to 4;
c4=0;
d=0 to 4;
$R^1$=alkyl radicals having 1 to 30 carbon atoms or aromatic hydrocarbon radicals having 6 to 30 carbon atoms, wherein the alkyl radicals are linear, branched, saturated, or unsaturated;
$R^{21}$=each independently identical or different divalent radicals selected from the group consisting of

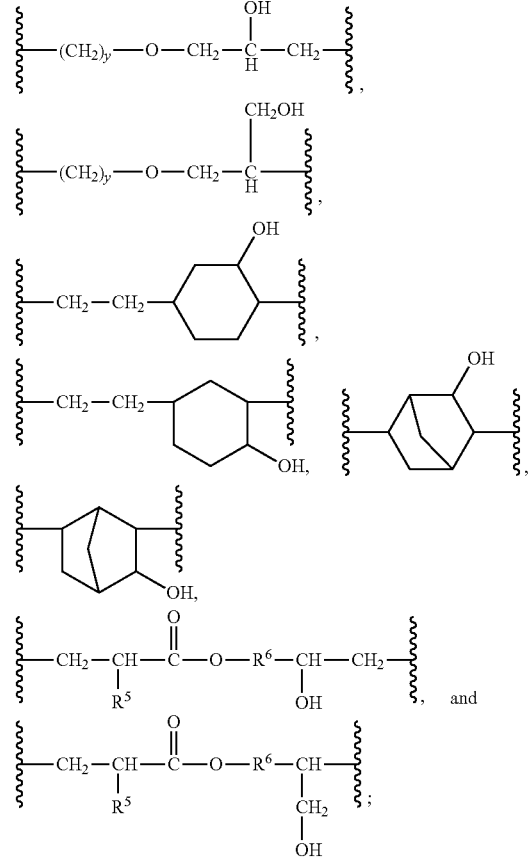

$R^4$=each independently identical or different groups, selected from the group consisting of acetoxy groups, methoxy groups, ethoxy groups, n-propoxy groups, isopropoxy groups, n-butoxy groups, tert-butoxy groups, and alkoxy groups derived from glycol radicals;

$R^5$=each independently identical or different radicals selected from the group consisting of hydrogen and hydrocarbon radicals;

$R^6$=each independently identical or different divalent hydrocarbon radicals optionally containing ether groups;

$R^7$=—NH—;

$R^8$=each independently identical or different radicals selected from the group consisting of methyl, ethyl, n-propyl, isopropyl, n-butyl, isobutyl, and tert-butyl;

$R^9$=each independently identical or different hydrocarbon radicals having 1 to 30 carbon atoms;

$R^{11}$=each independently identical or different radicals selected from the group consisting of alkyl radicals having at least one hydroxyl group and 1 to 6 carbon atoms;

m=1;

x=3; and y=2 to 18.

17. The Siloxane (A) according to claim 16, wherein $R^1$=methyl, ethyl, propyl, or phenyl;

$R^{21}$=each independently identical or different divalent radicals selected from the group consisting of

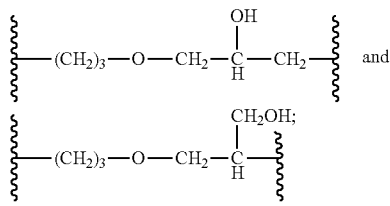 and $R^5$=each independently identical or different radicals selected from the group consisting of alkyl radicals having 1 to 6 carbon atoms, wherein the alkyl radicals are linear, branched, saturated, or unsaturated;

$R^6$=each independently identical or different divalent hydrocarbon radicals optionally containing ether groups, having 1 to 6 carbon atoms;

$R^8$=each independently identical or different radicals selected from the group consisting of methyl, ethyl, n-propyl, and isopropyl;

$R^9$=each independently identical or different hydrocarbon radicals having 1 to 30 carbon atoms;

$R^{11}$=2-hydroxyethyl and/or 2-hydroxypropyl;

m=1;

y=3, wherein for $R^4$, the glycol radicals, if present, are selected from the group consisting of propylene glycol, dipropylene glycol, tripropylene glycol, hexylene glycol, pentylene glycol, and butyldiglycol.

18. The siloxane (A) according to claim 2, wherein for condition (iv), a2≥2, a3≥1, and a4=0.

19. The composition according to claim 4, wherein the siloxane (B) is a siloxane that differs from the siloxane (A) precisely in that the conditions (v) and (vi) are applicable rather than the conditions (i) to (ii), and wherein the siloxane (C) is a siloxane that differs from the siloxane (A) precisely in that the conditions (vii) and (viii) are applicable rather than the conditions (i) and (ii).

20. The composition according to claim 5, wherein
a. the proportion by mass (% by weight) of the at least one siloxane (A) based on the total mass of the siloxanes is from 30% to 50%;
and/or
b. the proportion by mass (% by weight) of the at least one siloxane (B) based on the total mass of the siloxanes is from 1% to 10%;
and/or
c. the proportion by mass (% by weight) of the at least one siloxane (C) based on the total mass of the siloxanes is from 10% to 50%.

21. The composition of claim 3, wherein the composition has a content of greater than 0% and less than 3% by weight of one or more dialkanolamines and greater than 0% and less than 1% by weight of one or more amide amines that are tertiary amines.

22. The composition of claim 3, wherein the composition does not have a phase separation.

23. The siloxane (A) according to claim 1, obtained by reaction of compounds comprising at least one amide amine and at least one dialkanolamine,
wherein the at least one amide amine is at least one selected from the group consisting of 3-N,N-dimethylaminopropylcocoamide, 3-N,N-dimethylaminopropylstearamide, and 3-N,N-dimethylaminopropylpalmitamide; and
wherein the at least one dialkanolamine is at least one selected from the group consisting of N-methyldiethanolamine and N-methyldiisopropanolamine.

* * * * *

UNITED STATES PATENT AND TRADEMARK OFFICE
CERTIFICATE OF CORRECTION

PATENT NO. : 12,305,148 B2
APPLICATION NO. : 15/733704
DATED : May 20, 2025
INVENTOR(S) : Frauke Henning et al.

It is certified that error appears in the above-identified patent and that said Letters Patent is hereby corrected as shown below:

In the Claims

At Column 47, Claim 1, Line 42 currently reads:
"$R^{21}$ each"
And should be:
-$R^{21}$=each-;

At Column 47, Claim 1, Line 44 currently reads:
"$R^{22}$ each"
And should be:
-$R^{22}$=each-;

At Column 47, Claim 1, Lines 49-53 should read:

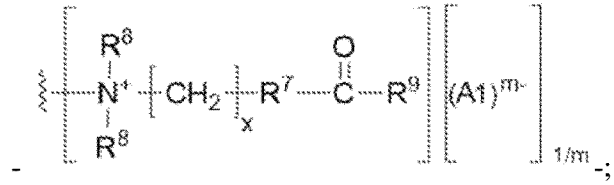

At Column 47, Claim 1, Lines 62-65 should read:

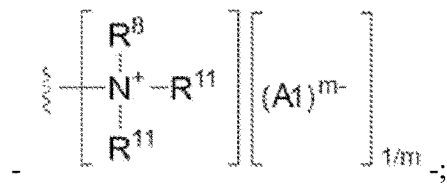

At Column 48, Claim 1, Line 15 currently reads:
"m 1 to 3; and"

Signed and Sealed this
Twenty-fifth Day of November, 2025

John A. Squires
*Director of the United States Patent and Trademark Office*

And should be:
-m = 1 to 3; and-;

At Column 50, Claim 16, Line 22 currently reads:
"b3=0,"
And should read:
-b3=0;-.